United States Patent
Papadopoulos et al.

(10) Patent No.: US 10,301,357 B2
(45) Date of Patent: May 28, 2019

(54) THERAPEUTICS FOR THE INDUCTION OF ENDOGENOUS STEROIDOGENESIS AND METHODS ASSOCIATED WITH THEIR IDENTIFICATION

(71) Applicant: THE ROYAL INSTITUTION FOR THE ADVANCEMENT OF LEARNING/MCGILL UNIVERSITY, Montreal (CA)

(72) Inventors: Vassilios Papadopoulos, Westmount (CA); Yasaman Aghazadeh, Toronto (CA); Jinjiang Fan, Côte Saint-Luc (CA)

(73) Assignee: THE ROYAL INSTITUTION FOR THE ADVANCEMENT OF LEARNING/MCGILL UNIVERSITY, Montreal, QC (CA)

( * ) Notice: Subject to any disclaimer, the term of this patent is extended or adjusted under 35 U.S.C. 154(b) by 236 days.

(21) Appl. No.: 14/897,782

(22) PCT Filed: May 21, 2014

(86) PCT No.: PCT/CA2014/050467
§ 371 (c)(1),
(2) Date: Dec. 11, 2015

(87) PCT Pub. No.: WO2014/197979
PCT Pub. Date: Dec. 18, 2014

(65) Prior Publication Data
US 2016/0108087 A1   Apr. 21, 2016

Related U.S. Application Data

(60) Provisional application No. 61/953,336, filed on Mar. 14, 2014, provisional application No. 61/834,993, filed on Jun. 14, 2013.

(51) Int. Cl.
| | |
|---|---|
| *C07K 7/08* | (2006.01) |
| *A61K 31/713* | (2006.01) |
| *C07K 14/705* | (2006.01) |
| *C07K 14/47* | (2006.01) |
| *C12P 33/00* | (2006.01) |
| *C12N 15/113* | (2010.01) |
| *G01N 33/50* | (2006.01) |
| *G01N 33/74* | (2006.01) |
| *C07K 7/06* | (2006.01) |
| *A61K 38/00* | (2006.01) |

(52) U.S. Cl.
CPC ............ *C07K 7/08* (2013.01); *A61K 31/713* (2013.01); *C07K 7/06* (2013.01); *C07K 14/47* (2013.01); *C07K 14/705* (2013.01); *C12N 15/113* (2013.01); *C12P 33/00* (2013.01); *G01N 33/5023* (2013.01); *G01N 33/5044* (2013.01); *G01N 33/743* (2013.01); *A61K 38/00* (2013.01); *C07K 2319/10* (2013.01); *C12N 2310/14* (2013.01); *C12N 2320/30* (2013.01)

(58) Field of Classification Search
CPC ........ C07K 7/08; C07K 14/47; C07K 14/705; A61K 31/713; C12N 15/113; C12P 33/00; G01N 33/5023; G01N 33/5044; G01N 33/743
See application file for complete search history.

(56) References Cited

U.S. PATENT DOCUMENTS

| | | | |
|---|---|---|---|
| 5,525,491 A * | 6/1996 | Huston | C07K 16/00 435/252.3 |
| 7,803,351 B2 | 9/2010 | Sharma et al. | |
| 2005/0042603 A1* | 2/2005 | Wang | C07K 14/005 435/5 |
| 2008/0274962 A1* | 11/2008 | Shoshan-Barmatz | C07K 14/4747 514/12.2 |

FOREIGN PATENT DOCUMENTS

| | | | | |
|---|---|---|---|---|
| WO | WO2002/46767 | * | 6/2002 | ............ G01N 33/68 |
| WO | 2006095347 | | 9/2006 | |
| WO | WO 2007/043049 | * | 4/2007 | |
| WO | 2013143026 | | 10/2013 | |
| WO | WO2013/143026 | * | 10/2013 | |
| WO | 20070043049 A1 | | 4/2017 | |

OTHER PUBLICATIONS

Chen et al., Adv Drug Deliv Rev. Oct. 15, 2013; 65(10): 1357-1369.*
Schwarze et al., trends in Cell Biology (vol. 10) Jul. 2000, pp. 290-295.*
Aghazdeh, Y. et al. Hormone-induced 14-3-3gamma adaptor protein regulates steroidogenic acute regulatory protein activity and steroid biosynthesis in MA-10 Leydig cells. J. Biol. Chem. (2012).

(Continued)

*Primary Examiner* — Karlheinz R. Skowronek
*Assistant Examiner* — Joseph Fischer

(57) ABSTRACT

The present disclosure provides agents capable of promoting endogenous steroid production (such as endogenous testosterone production) without altering the endogenous luteinizing hormone. The present disclosure also provides associated therapeutic methods as well as screening assays for identifying further therapeutic agents for the prevention, treatment and/or alleviations of symptoms associated with hypogonadism.

20 Claims, 19 Drawing Sheets

Specification includes a Sequence Listing.

(56) References Cited

OTHER PUBLICATIONS

Aitken, A. 14-3-3 proteins: a historic overview. Semin. Cancer Biol. 16, 162-172 (2006).

Fredriksson, S. et al. Protein detection using proximity-dependent DNA ligation assays. Nat. Biotechnol. 20, 473-477 (2002).

Gegenbauer, K., Elia, G., Blanco-Fernandez, A., & Smolenski, A. Regulator of G-protein signaling 18 integrates activating and inhibitory signaling in platelets. Blood 119, 3799-3807 (2012).

Gwynne, J.T. & Strauss, J.F., III The role of lipoproteins in steroidogenesis and cholesterol metabolism in steroidogenic glands. Endocr. Rev. 3, 299-329 (1982).

Horvath, J.E., Toiler, G.L, Schally, A.V., Bajo, A.M., & Groot, K. Effect of long-term treatment with low doses of the LHRH antagonist Cetrorelix on pituitary receptors for LHRH and gonadal axis in male and female rats. Proc. Natl. Acad. Sci. U. S. A 101, 4996-5001 (2004).

Kramer, B., Rarey, M., & Lengauer, T. CASP2 experiences with docking flexible ligands using FlexX. Proteins Suppl 1, 221-225 (1997).

Naghara, H. et al. Transduction of full-length TAT fusion proteins into mammalian cells: TAT-p27Kip1 induces cell migration. Nat. Med. 4, 1449-1452 (1998).

Perheentupa, A. & Huhtaniemi, I. Aging of the human ovary and testis. Mol. Cell Endocrinol. 299, 2-13 (2009).

Ritchie, D.W. & Venkatraman, V. Ultra-fast FFT protein docking on graphics processors. Bioinformatics. 26, 2398-2405 (2010).

Trott, O. & Olson, A.J. AutoDock Vina: improving the speed and accuracy of docking with a new scoring function, efficient optimization, and multithreading. J. Comput. Chem. 31, 455-461 (2010).

Yaffe, M.B. et al. The structural basis for 14-3-3:phosphopeptide binding specificity. Cell 91, 961-971 (1997).

Examination Report No. 1 for Australia Application 2014280805, Published Jan. 7, 2016.

Tzu-An Liu et al., 14-3-3 Overexpression Contributes to Epithelial-Mesenchymal Transition of Hepatocellular Carcinoma, vol. 8, No. 3, Mar. 6, 2013, p. e57968, XP055306238.

Supplementary European Search Report in related European Application No. 14810382.3, dated Oct. 11, 2016.

\* cited by examiner

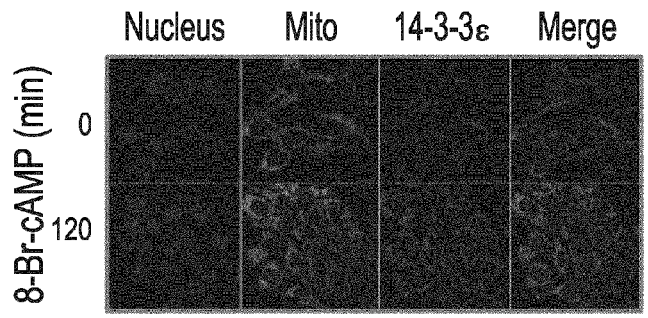
Figure 1a
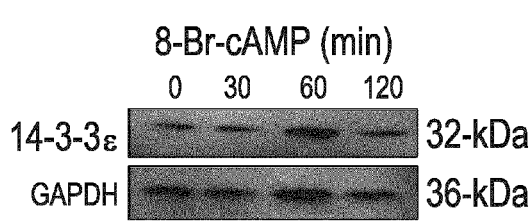
Figure 1b1
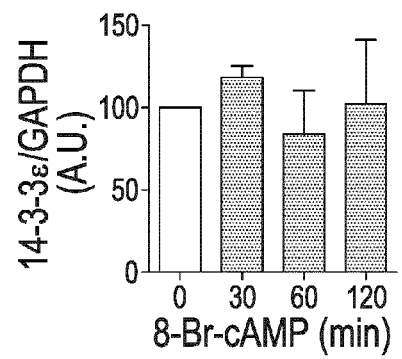
Figure 1b2
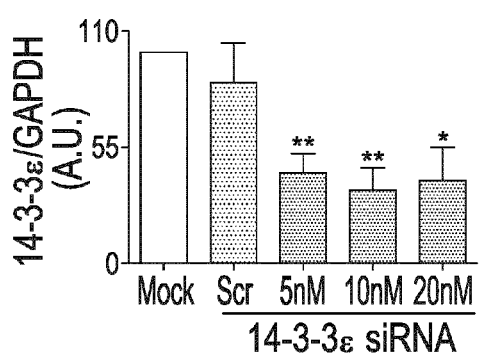
Figure 1c1
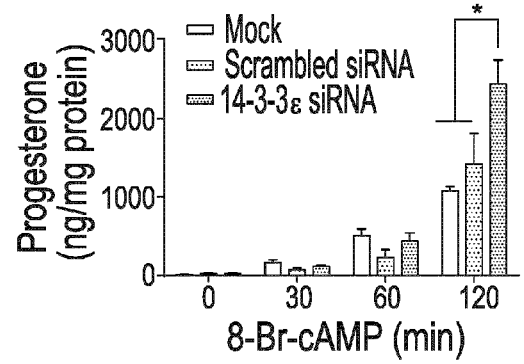
Figure 1d
Figure 1c2

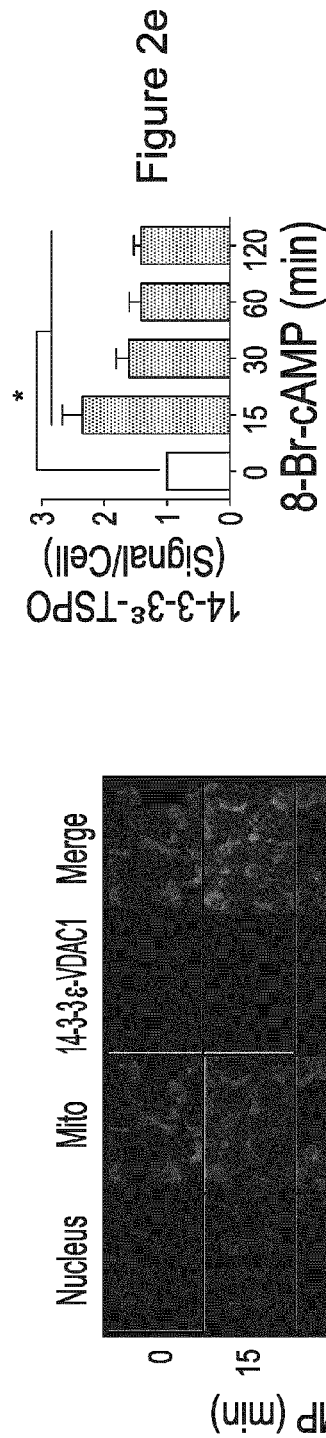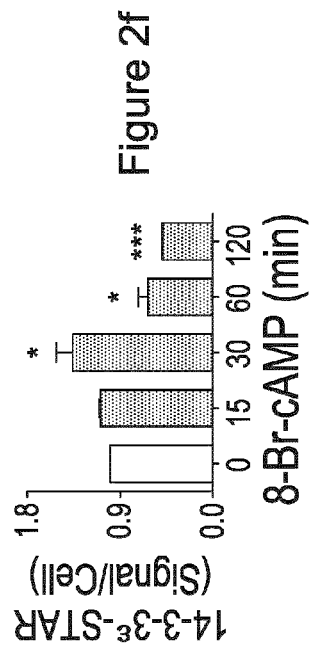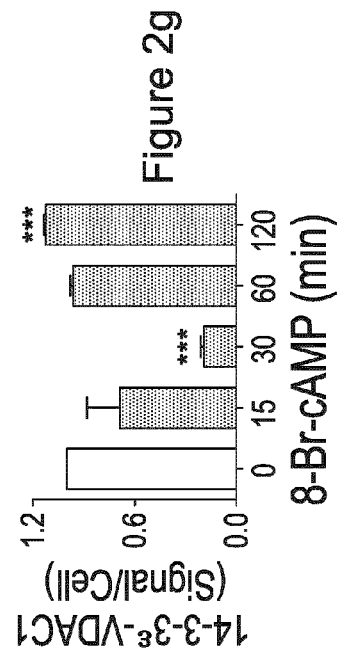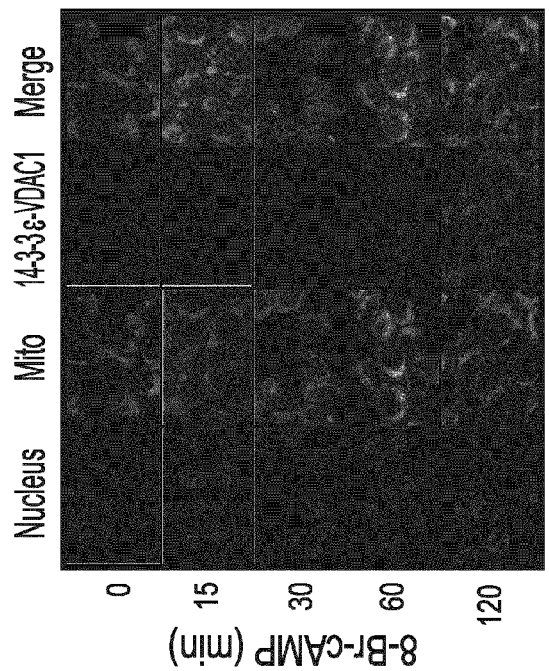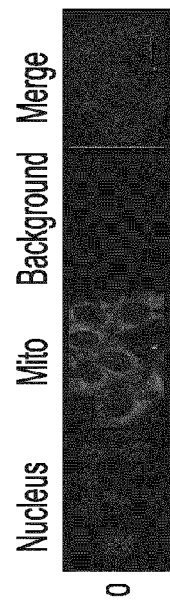

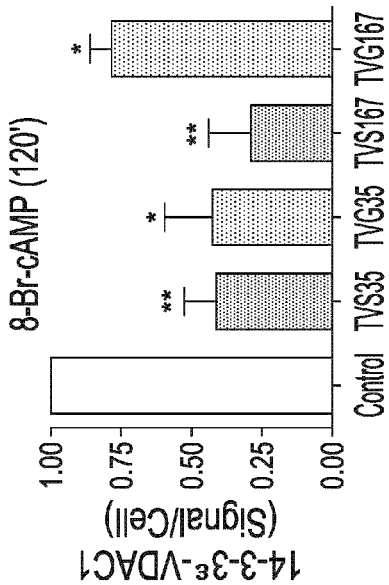
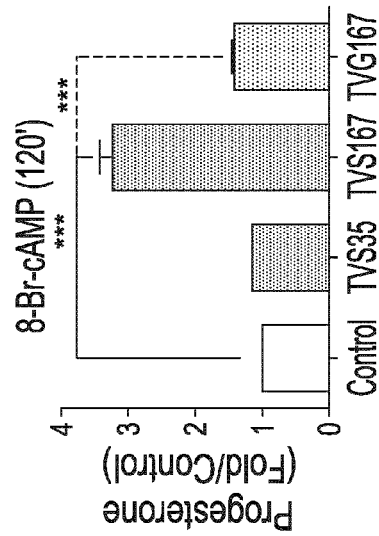
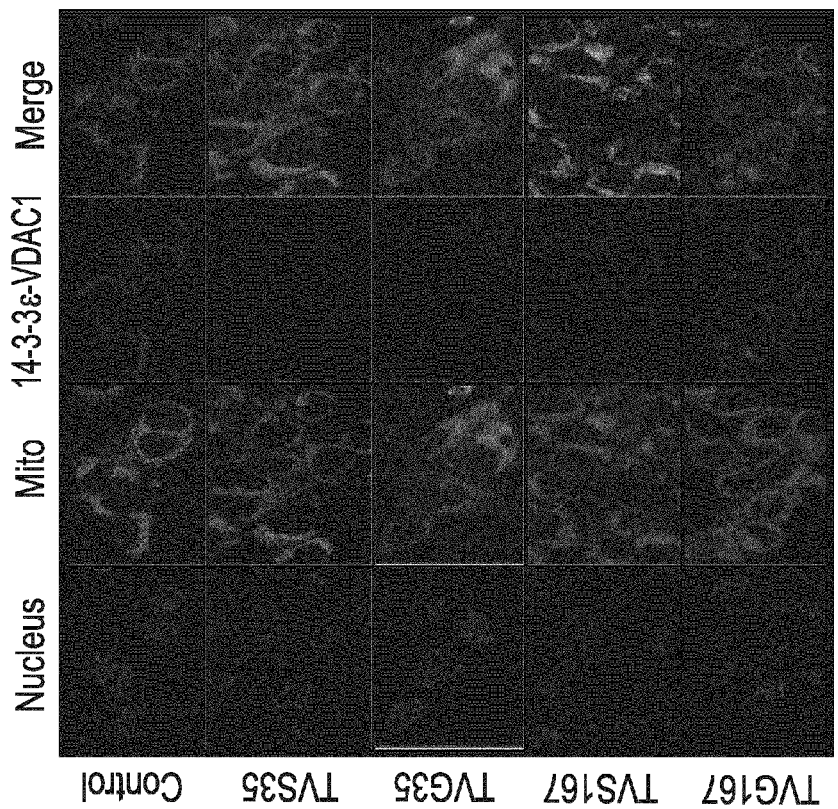
Figure 3a
Figure 3b
Figure 3c

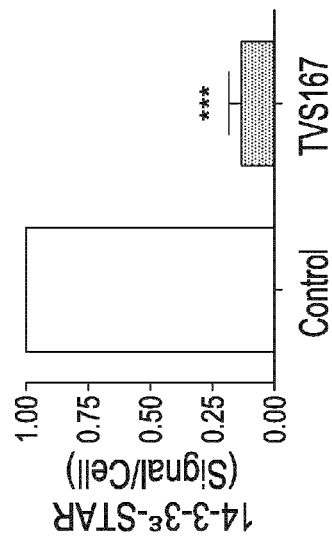
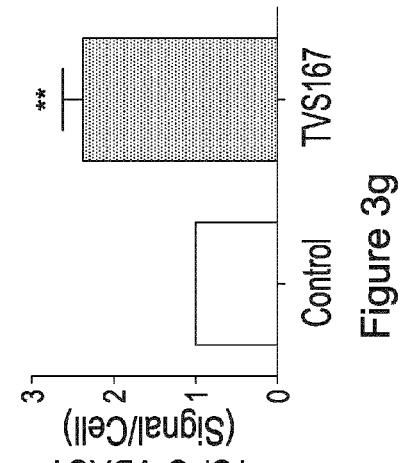
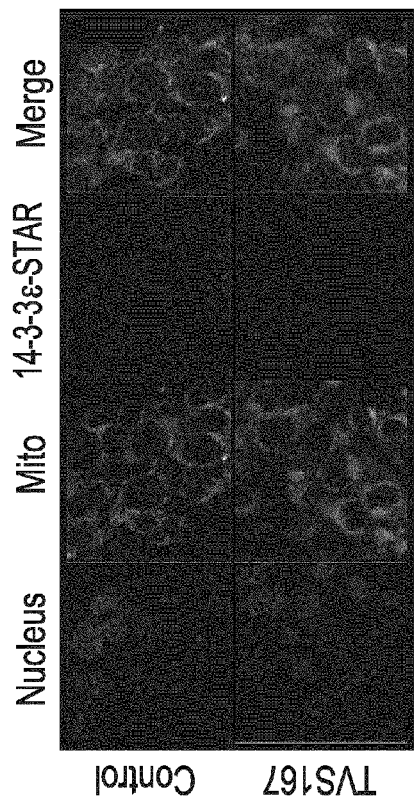
Figure 3d
Figure 3e
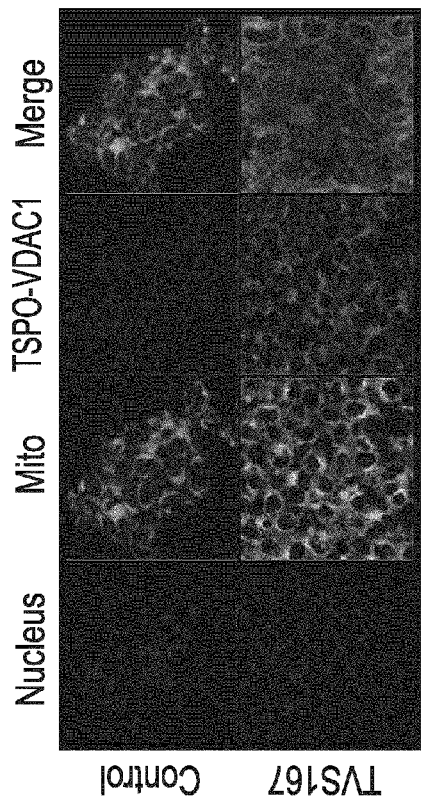
Figure 3f
Figure 3g

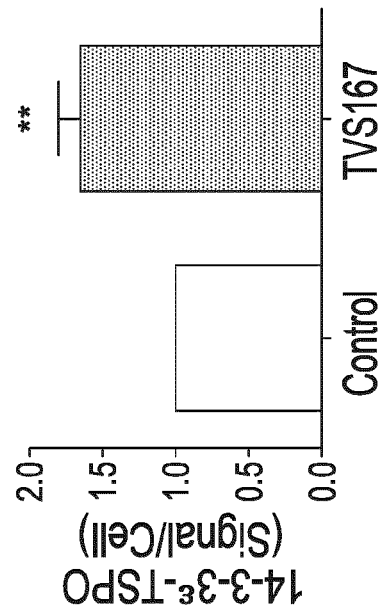
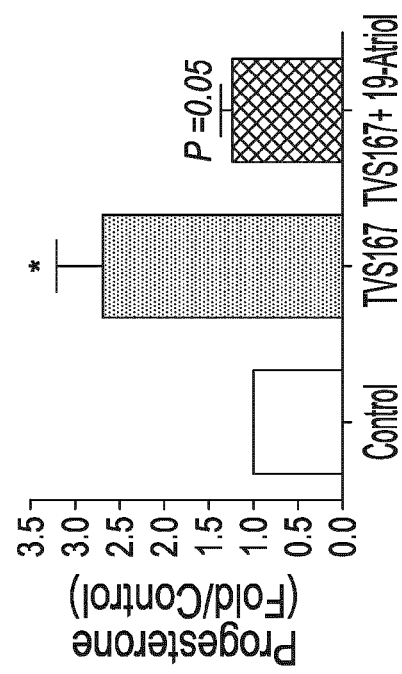
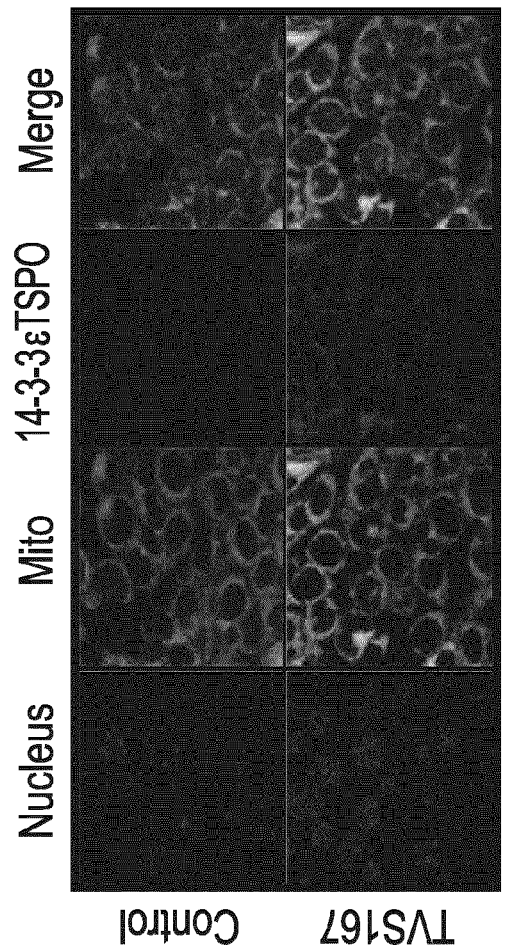
Figure 3h
Figure 3i
Figure 3j

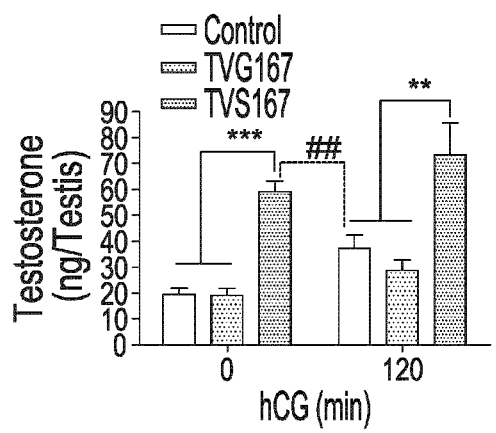
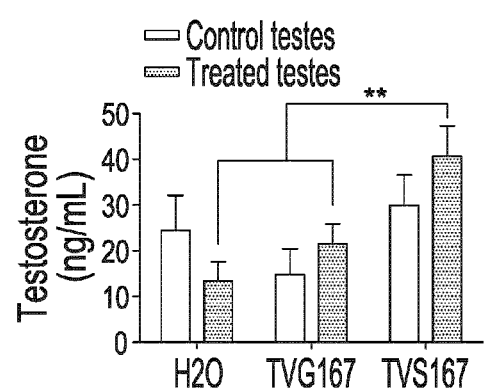
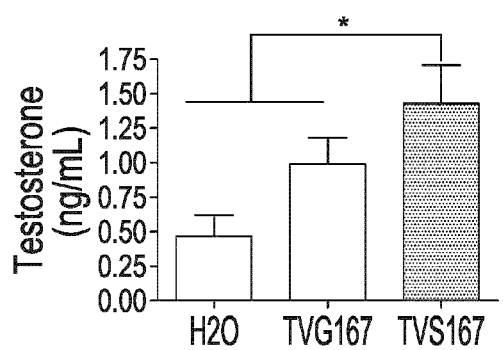
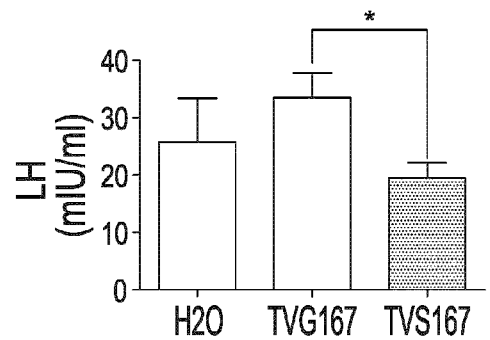
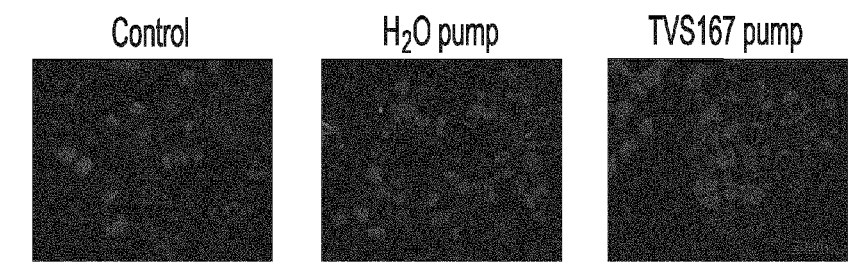
Figure 4e

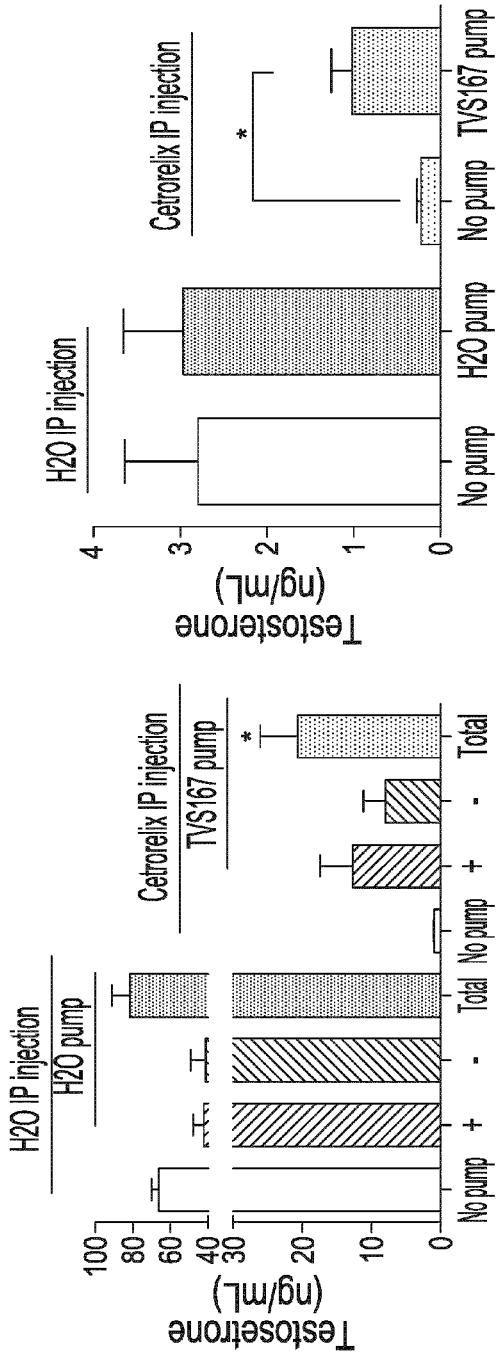
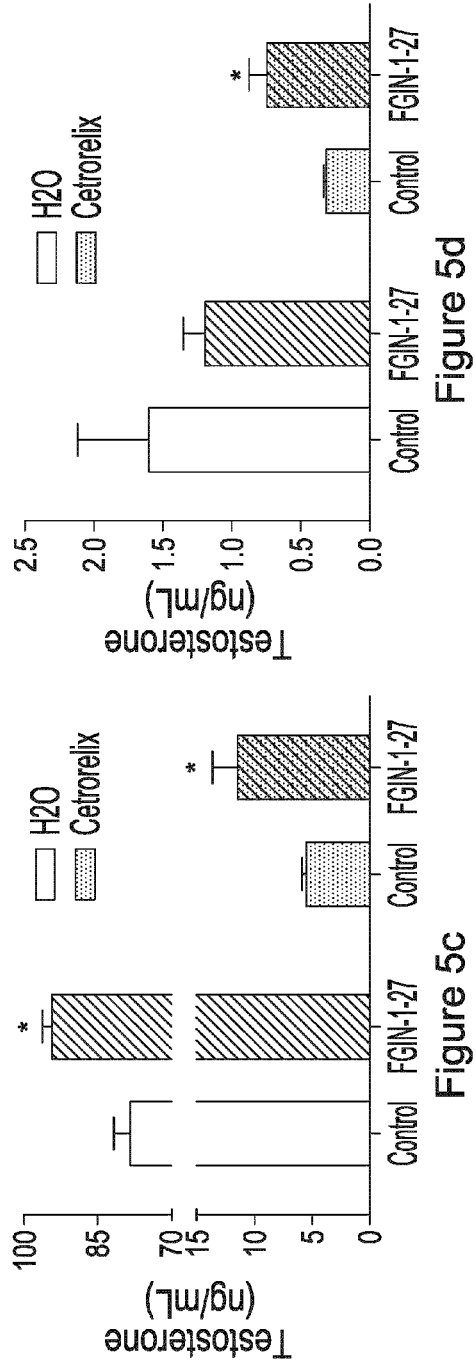
Figure 5a, Figure 5b, Figure 5c, Figure 5d

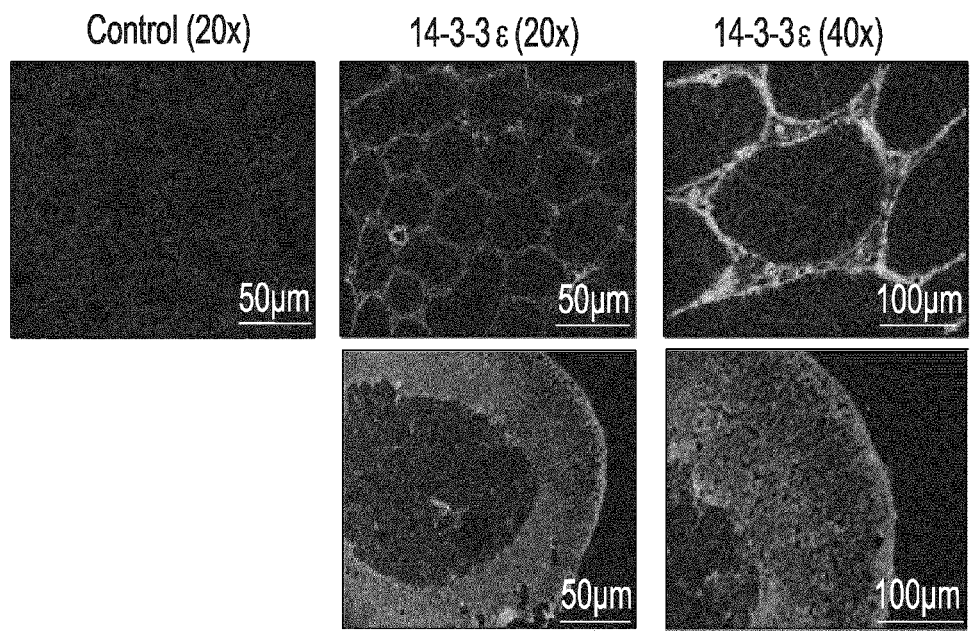
Figure 7a
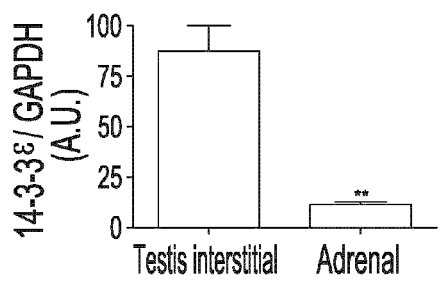
Figure 7b1
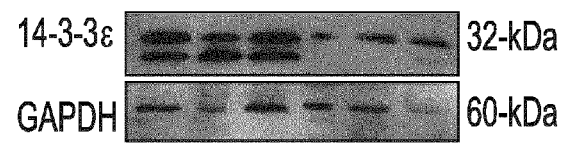
Figure 7b2
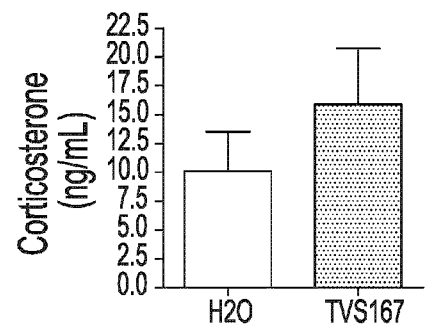
Figure 7c

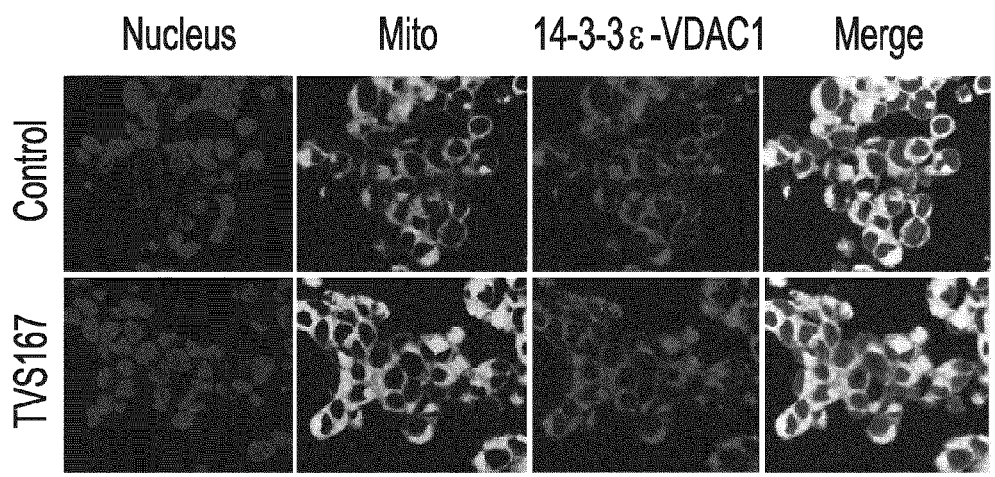
Figure 7e1
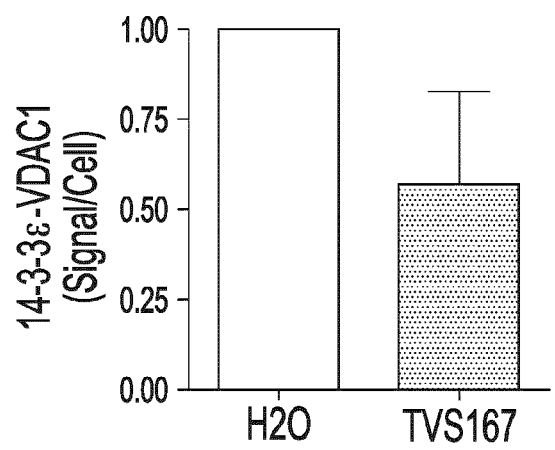
Figure 7e2

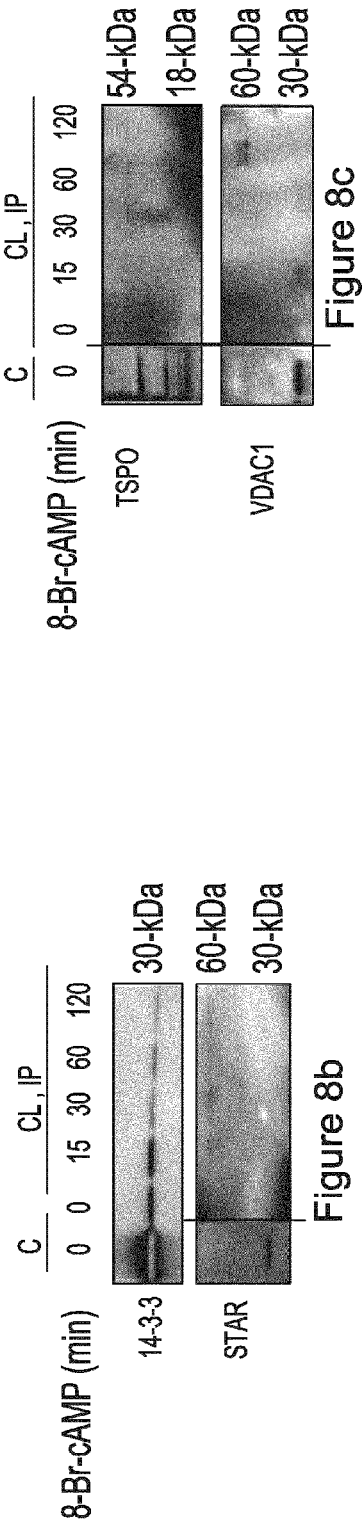

14-3-3ε

| | |
|---|---|
| Mus | MDDREDLVYQAKLAEQAERYDEMVESMKKVAGMDVELTVEERNLLSVAYKNVIGARRASW |
| Homo | MDDREDLVYQAKLAEQAERYDEMVESMKKVAGMDVELTVEERNLLSVAYKNVIGARRASW |
| Rattus | MDDREDLVYQAKLAEQAERYDEMVESMKKVAGMDVELTVEERNLLSVAYKNVIGARRASW |

| | |
|---|---|
| Mus | RIISSIEQKEENKGGEDKLKMIREYRQMVETELKLICCDILDVLDKHLIPAANTGESKVF |
| Homo | RIISSIEQKEENKGGEDKLKMIREYRQMVETELKLICCDILDVLDKHLIPAANTGESKVF |
| Rattus | RIISSIEQKEENTGGEDKLKMIREYRQMVETELKLICCDILDVLDKHLIPAANTGESKVS |

| | |
|---|---|
| Mus | YYKMKGDYHRYLAEFATGNDRKEAAENSLVAYKAASDIAMTELPPTHPIRLGLALNFSVF |
| Homo | YYKMKGDYHRYLAEFATGNDRKEAAENSLVAYKAASDIAMTELPPTHPIRLGLALNFSVF |
| Rattus | YYYMKGDYHRYLAEFATGNDRKEAAENSLVAYKAASDIAMTELPPTHPIRLGLALNFSVF |

| | |
|---|---|
| Mus | YYEILNSPDRACRLAKAAFDDAIAELDTLSEESYKDSTLIMQLLRDNLTLWTSDMQGDGE |
| Homo | YYEILNSPDRACRLAKAAFDDAIAELDTLSEESYKDSTLIMQLLRDNLTLWTSDMQGDGE |
| Rattus | YYEILNSPDRACRLAKAAFDDAIAELDTLSEESYKDSTLIMQLLRDNLTLWTSDMQGDGE |

| | | |
|---|---|---|
| Mus | EQNKEALQDVEDENQ | (SEQ ID NO:17) |
| Homo | EQNKEALQDVEDENQ | (SEQ ID NO:18) |
| Rattus | EQNKEALQDVEDENQ | (SEQ ID NO:19) |

Figure 13a

VDAC1

```
Mus     MAVPPTYADLGKSARDVFTKGYGFGLIKLDLKTKSENGLEFTSSGSANTETTKVNGSLET
Rattus  MAVPPTYADLGKSARDVFTKGYGFGLIKLDLKTKSENGLEFTSSGSANTETTKVNGSLET
Homo    MAVPPTYADLGKSARDVFTKGYGFGLIKLDLKTKSENGLEFTSSGSANTETTKVTGSLET
        ****************************************************  ****

Mus     KYRWTEYGLTFTEKWNTDNTLGTEITVEDQLARGLKLTFDSSFSPNTGKKNAKIKTGYKR
Rattus  KYRWTEYGLTFTEKWNTDNTLGTEITVEDQLARGLKLTFDSSFSPNTGKKNAKIKTGYKR
Homo    KYRWTEYGLTFTEKWNTDNTLGTEITVEDQLARGLKLTFDSSFSPNTGKKNAKIKTGYKR
        ************************************************************

Mus     EHINLGCDVDFDIAGPSIRGALVLGYEGWLAGYQMNFETSKSRVTQSNFAVGYKTDEFQL
Rattus  EHINLGCDVDFDIAGPSIRGALVLGYEGWLAGYQMNFETSKSRVTQSNFAVGYKTDEFQL
Homo    EHINLGCDMDFDIAGPSIRGALVLGYEGWLAGYQMNFETAKSRVTQSNFAVGYKTDEFQL
        ********:*****************************:*********************

Mus     HTNVNDGTEFGGSIYQKVNKKLETAVNLAWTAGNSNTRFGIAAKYQVDPDACFSAKVNNS
Rattus  HTNVNDGTEFGGSIYQKVNKKLETAVNLAWTAGNSNTRFGIAAKYQVDPDACFSAKVNNS
Homo    HTNVNDGTEFGGSIYQKVNKKLETAVNLAWTAGNSNTRFGIAAKYQIDPDACFSAKVNNS
        *********************************************:************

Mus     SLIGLGYTQTLKPGIKLTLSALLDGKNVNAGGHKLGLGLEFQA   (SEQ ID NO:20)
Rattus  SLIGLGYTQTLKPGIKLTLSALLDGKNVNAGGHKLGLGLEFQA   (SEQ ID NO:22)
Homo    SLIGLGYTQTLKPGIKLTLSALLDGKNVNAGGHKLGLGLEFQA   (SEQ ID NO:21)
        ******************************************
```

Figure 13b

THERAPEUTICS FOR THE INDUCTION OF ENDOGENOUS STEROIDOGENESIS AND METHODS ASSOCIATED WITH THEIR IDENTIFICATION

CROSS-REFERENCE TO RELATED APPLICATIONS AND DOCUMENTS

This application claims priority from U.S. provisional patent application Ser. No. 61/834,993 filed on Jun. 14, 2013 and 61/953,336 filed on Mar. 14, 2014, both of which are incorporated by reference in their entirety. This application also comprises a sequence listing which has been filed electronically. The content of such electronic submission is incorporated by reference in its entirety.

TECHNOLOGICAL FIELD

The present disclosure concern peptide-based agents promoting endogenous steroidogenesis and particularly the production of testosterone as well as associated therapeutic applications especially suited for the prevention, treatment and/or alleviation of symptoms associated with hypogonadism. The peptide-based agents comprise 14-3-3ε binding motifs and are shown to limit or impede the association between the 14-3-3ε protein and the VDAC1 protein. The present disclosure also provides corresponding screening assays based for identifying further therapeutic agents for promoting endogenous steroidogenesis especially suited for the prevention, treatment and/or alleviation of symptoms associated with hypogonadism.

BACKGROUND

Reduced serum testosterone (T) is common among subfertile and infertile young men, including most men diagnosed with idiopathic infertility. Reduced T is also common in aging men, with T levels declining at age 40 and been low in the majority of men older than 60. Reduced T is often associated with mood changes, fatigue, depression, decreased lean body mass, reduced bone mineral density, increased visceral fat, metabolic syndrome, decreased libido and reduced sexual function. T replacement therapy (TRT) is used clinically to restore T levels. TRT can treat symptoms associated with low T. However, TRT may increase the risk and aggressiveness of prostate cancer, augment the incidence of adverse cardiovascular events, favor obesity and depression and even increase the rate of mortality in patients. Therefore is not recommended for patients at high risk of such diseases. Moreover, long-term TRT can suppress luteinizing hormone (LH) production, making this approach inappropriate for men who wish to have children. Fluctuating T levels, skin irritation, and T transfer to others through skin contact are additional disadvantages of TRT. The molecular mechanisms that govern androgen formation in testicular Leydig cells remain unclear. Identification of these mechanisms will facilitate development of new approaches for inducing endogenous T synthesis voiding exogenous T treatment.

T production is regulated by LH and its secondary messenger, cAMP. Cholesterol import from cytosolic sources into mitochondria is a hormone-sensitive and rate-limiting step of steroidogenesis. Cholesterol is cleaved into pregnenolone by CYP11A1 in mitochondria, and steroidogenesis begins. Cholesterol import into mitochondria is mediated by a hormone-induced multiprotein complex called the transduceosome, which is composed of cytosolic and outer mitochondrial membrane (OMM) proteins that control the rate of cholesterol entry into the OMM. These proteins include the cytosolic mitochondria-targeted, hormone-induced steroidogenic acute regulatory protein (STAR), the OMM high-affinity cholesterol-binding protein translocator protein (TSPO), which contains a cytosolic cholesterol recognition/interaction domain (CRAC) and the OMM voltage-dependent anion channel protein (VDAC1). Recent studies shed light on the importance of interactions between STAR, TSPO and VDAC1, suggesting that cholesterol import into mitochondria relies on the function and physical interactions between components of the transduceosome. The nature and dynamics of transduceosome protein-protein interactions remain unknown.

The 14-3-3 family of adaptor proteins were recently shown to have binding motifs on important functional sites in STAR, TSPO, and VDAC1 and 14-3-3γ was identified as a regulator of STAR activity. However this hormone-induced 14-3-3 isoform was shown to function in a transient manner at the initiation of steroidogenesis, to delay the maximum STAR activity. Indeed, the function of 14-3-3γ is terminated as it dissociates from STAR, allowing for maximal steroid production. In these studies, the levels of the 14-3-3 family ε isoform, were found to be increased in Leydig cell mitochondria during steroidogenesis. This isoform mediates in a tissue/target-specific manner, cell functions such as neural development, adipocyte differentiation, protein trafficking, cell cycle, apoptosis and cell signaling. Levels of 14-3-3ε, formerly known as mitochondrial import stimulating factor 25, are also high in human testes but its function in this tissue is unknown.

It would be desirable to be provided with a therapeutic agent capable of upregulating endogenous steroid production, such as testosterone production, without altering luteinizing hormone levels, to avoid or limit the side-effects listed above. It would also be desirable to be provided with screening assays for determining if a putative agent is capable of upregulating endogenous steroid production.

SUMMARY

One aim of the present disclosure is to provide agents capable of promoting endogenous steroidogenesis (and particularly the production of testosterone) without altering the endogenous production of the luteinizing hormone. These agents can be used for the prevention, treatment and/or alleviation of symptoms associated with hypogonadism. As it will be shown herein, isolated peptides comprising the amino acid sequence RVTQSNF (SEQ ID NO: 5), a 14-3-3ε binding motif, can limit or impede the interaction between the 14-3-3ε protein and the VDAC1 protein and, consequently favor endogenous steroidogenesis (such as testosterone production). The present disclosure also provides corresponding screening assays based for identifying further therapeutic agents for promoting endogenous steroidogenesis especially suited for the prevention, treatment and/or alleviation of symptoms associated with hypogonadism.

According to a first aspect, the present disclosure provides an isolated peptide having the amino acid sequence RVTQSNF (SEQ ID NO: 5). In an embodiment, the isolated peptide has the amino acid sequence SKSRVTQSNFAVG (SEQ ID NO: 30). In an another embodiment, the serine residue at position 5 of SEQ ID NO: 5 or at position 8 of SEQ ID NO: 30 of the isolated peptide is phosphorylated.

According to a second aspect, the present disclosure provides a chimeric peptide having the isolated peptide described herein fused to a cell penetrating peptide. In an embodiment, the cell penetrating peptide is from a TAT protein and can have the amino acid sequence YGRK-KRRQRRR (SEQ ID NO: 29). In another embodiment, the carboxy terminus of the cell penetrating peptide is fused to the amino terminus of the isolated peptide. In still another embodiment, the isolated peptide is fused to the cell penetrating peptide by a linker. In still another embodiment, the linker can comprise at least one amino acid, such as, for example, a glycine residue.

According to a third aspect, the present disclosure provides a delivery system comprising (i) the isolated peptide described herein or the chimeric peptide described herein and (ii) a cell penetration enhancer.

According to a fourth aspect, the present disclosure provides the isolated peptide described herein, the chimeric peptide described herein or the delivery system described herein for use in therapy.

According to a fifth aspect, the present disclosure provides a method for promoting the endogenous production of a steroid in a cell. Broadly, the method comprises contacting the cell with at least one of the isolated peptide described herein, the chimeric peptide described herein, the delivery system described herein or a nucleic acid molecule impeding the expression of a 14-3-3ε protein. The methods described herein if designed to promote the endogenous production of the steroid in the cell. In an embodiment, the nucleic acid molecule encodes a siRNA specific or comprises a combination of siRNAs specific for a transcript encoding a 14-3-3ε protein. In an embodiment, the steroid is testosterone. In still another embodiment, the cell is in vitro. In yet another embodiment, the cell is in vivo and the method further comprises administering the isolated peptide, the chimeric peptide, the delivery system or the nucleic acid molecule to a subject in need thereof comprising the cell. In some embodiments, the subject is a mammal and/or a male. In yet another embodiment, the cell is from a testis, such as, for example a Leydig cell. In yet a further embodiment, the method is for the prevention, treatment and/or alleviation of symptoms of a condition associated with hypogonadism. Conditions associated with hypogonadism include, but are not limited to infertility, aging, decreased libido, sexual dysfunction, altered mood, fatigue, decreased lean body mass, decreased bone mineral density, increased visceral fat or metabolic syndrome.

According to a sixth aspect, the present disclosure provides the use of the isolated peptide described herein, the chimeric peptide described herein, the delivery system described herein or a nucleic acid molecule impeding the expression of a 14-3-3ε protein for promoting the endogenous production of a steroid in a cell. In an embodiment, the nucleic acid molecule is a siRNA or comprises a combination of siRNAs specific for a transcript of a 14-3-3ε protein. In another embodiment, the steroid is testosterone. In a further embodiment, the cell is in a subject such as, for example, a mammal and/or a male. In another embodiment, the cell is from a testis, such as, for example, a Leydig cell. In yet a further embodiment, the use is for the prevention, treatment and/or alleviation of symptoms of a condition associated with hypogonadism. Conditions associated with hypogonadism include, but are not limited to infertility, aging, decreased libido, sexual dysfunction, altered mood, fatigue, decreased lean body mass, decreased bone mineral density, increased visceral fat or metabolic syndrome.

According to a seventh aspect, the present disclosure provides a method for determining the usefulness of an agent for promoting endogenous steroid production in a cell. Broadly, the method comprises: (a) combining the agent, a 14-3-3ε protein and a VDAC1 protein; (b) determining if the agent promotes or impedes the formation and/or stability of a complex between the 14-3-3ε protein and the VDAC1 protein; and (c) characterizing the agent (i) as being useful for promoting endogenous steroid production if the agent impedes the formation and/or stability of the complex or (ii) as lacking utility to promote endogenous steroid production if the agent promotes the formation and/or stability of the complex. In an embodiment, the steroid is testosterone. In another embodiment, the combining step is conducted in vitro in a cell, such as, for example, a MA-10 cell. In a further embodiment, the combining step is conducted ex vivo in a tissue, such as, for example, an isolated testis. In yet another embodiment, the combining step is conducted in an animal. In still another embodiment, the cell is from or in a testis, such as, for example, a Leydig cell.

BRIEF DESCRIPTION OF THE DRAWINGS

Having thus generally described the nature of the invention, reference will now be made to the accompanying drawings, showing by way of illustration, a preferred embodiment thereof, and in which:

FIG. 1 illustrates that 14-3-3ε is a negative regulator of steroidogenesis. (a) Immunohistochemistry (ICC) indicates that 14-3-3ε is present in MA-10 cells (third column) and that this protein partially localizes with mitochondria (second column). MA-10 nucleus is also shown (first column). Results are shown with respect to the time of incubation of the cells with 8-Br-cAMP in minutes (0=first row, 120=second row) (b1) Immunoblot results of MA-10 cells stimulated with 8-Br-cAMP for indicated time points (in minutes) show 14-3-3ε expression (first row) and quantification relative to GAPDH control protein (second row). (b2) Immunoblot analysis corresponding to the immunoblot of FIG. 1$b1$. Results are shown as the ratio of 14-3-3ε to GAPDH protein in function of incubation time (in minutes) with 8-Br-cAMP. (c1) Immunoblot analysis indicating the levels of 14-3-3ε protein compared to GAPDH in MA-10 cells in the absence of siRNA (mock), transfected with scrambled (Scr) siRNA as negative and positive control, respectively, or transfected with a mixture of 14-3-3ε specific siRNA at different concentrations (20 nM, 10 nM, or 5 nM). * $P<0.05$ and ** $P<0.01$ (c2) Immunoblot indicating the levels of 14-3-3ε protein and GAPDH in MA-10 cells in the absence of siRNA (mock), transfected with scrambled (Scr) siRNA as negative and positive control, respectively, or transfected with a mixture of 14-3-3ε specific siRNA at different concentrations (20 nM, 10 nM, or 5 nM). (d) MA-10 cells were transfected with 10 nM 14-3-3ε siRNA and further stimulated with 8-Br-cAMP for 0, 30, 60, and 120 min, and progesterone levels were measured at each time point. Results are shown for the mock treatment (white bars), the treatment with the scrambled siRNA (grey bars) and the treatment with the 14-3-3ε siRNA (black bars). * $P<0.05$

FIG. 3 illustrates that blocking the interaction between 14-3-3ε and VDAC1 negates the regulatory role of 14-3-3ε in steroidogenesis. (a, b) The Duolink assay was performed to measure protein-protein interactions between 14-3-3ε and endogenous VDAC1 in untreated MA-10 cells (control) or cells treated with the TVS35, TVG35, TVS167, or TVS167 peptides, after 8-Br-cAMP (120 min) treatment which induces maximum 14-3-3ε-VDAC1 interaction (third column of each panel). Staining of nucleus (first column of each panel) and mitochondrial (second column of each panel) are also shown. Immunohistochemistry is whon in (a) while the corresponding analysis is shown in (b, *=, =). (c) Progesterone levels in control MA-10 cells or cells treated with TVS35, TVS167, or TVS167 were measured after 8-Br-cAMP (120 min) treatment. Levels of progesterone were normalized to protein content and further compared to the levels in control cells, as fold increase. * P<0.001 (d, e, f, g, j). The impact of blocking interactions between 14-3-3ε-VDAC1 on other transduceosome protein-protein interactions was studied in the presence of TVS167. MA-10 cells were treated with TVS167 and 8-Br-cAMP (120 min). The interactions between 14-3-3ε-STAR (d, e in which * P<0.001), TSPO-VDAC1 (f, g in which  P<0.01) and 14-3-3ε-TSPO (h, I in which ** P<0.01) were measured, as endogenous protein-protein interactions. Histograms show the sum of protein-protein interactions in Z-stacks as signal/cell ratio. (j) The physiological impact of the increase in 14-3-3ε-TSPO interactions on cholesterol binding to TSPO was studied. Progesterone levels in control (untreated), TVS167-treated, and combination 19-Atriol/TVS167-treated MA-10 cells were measured after 8-Br-cAMP stimulation (120 min). * P<0.05.

FIG. 4 shows the effect of ex vivo and in vivo administration of TVS167 on T production. (a) Testes dissected from adult Sprague-Dawley rats were cultured in media supplemented with or without TVG167 or TVS167 and/or hCG (120 min). T levels were measured. Results are shown as T levels (in ng/testes) for control treatment (white bars), treatment with TVG167 (gray bars) or treatment with TVS167 (black bars) before and after hCG treatment.  P<0.01, * P<0.001, ## P=0.01) (b, c, d) Adult Sprague-Dawley rats were injected in one testis with water or 150 ng TVG167 or TVS167. A pump releasing $H_2O$, 75 ng/24 h TVG167, or 75 ng/24 h TVS167 was connected to the injected testis. Animals were dissected after 24 hrs. Intratesticular T levels were measured (ng/mL) in treated (black bars) and control (white bars) testes (b in which ** P<0.01). Serum T levels (in ng/mL in c in which * P<0.05) and serum LH levels (in mIU/mL in d in which * P<0.05) were also measured in $H_2O$-treated (white bars), TVG167-treated (gray bars) and TVS-167-treated (black bars) animals. (e) Duolink assay was performed on the testes sections. Immunofluorescence images show the merge of nucleus channel and protein-protein interaction channel indicating that, in the presence of TVS167 peptide, the interactions of 14-3-3ε and VDAC1 in rat testes are removed.

FIG. 5 shows that the effect of TVS167 in vivo is LH-independent. (a, b) Adult Sprague-Dawley rats were given i.p. injections of $H_2O$ or Cetrorelix (0.4 mg/day). Animals were either dissected on day 4 (no pump) or treated with $H_2O$ (if given H2O i.p.) or TVS167 (if given Cetrorelix i.p.) through a bolus injection and pump installation to one testis and dissected 24 hrs after pump installation. T levels (provided in ng/mL) in the intratesticular fluid (a in which * P<0.05) of testis connected to a pump (+), not connected to a pump (−), or both testes (no pump and Total) and in serum were measured (b in which * P<0.05). (c, d) Adult Sprague-Dawley rats were injected i.p. with either $H_2O$ or Cetrorelix for 0-4 days and on day 4, one testis per animal was given a bolus injection of 8.5 μg FGIN-1-27 to induce acute steroidogenesis in the absence or presence of LH signaling. T levels (provided in ng/mL) in intratesticular (c in which * P<0.05) and plasma (d in which * P<0.05 were measured in animal treated with $H_2O$ (white bars) or Cetrorelix (grey bars) 2 hrs post injection, showing a significant increase.

FIG. 8 illustrates the characteristics of the 14-3-3ε binding motifs. (a) TSPO, STAR and VDAC1 each contain 2 to 3 in silico predicted 14-3-3 binding motif as indicated. The amino acid sequence of these motifs is shown based on the sequence homology with mode I (RSXpSXP or SEQ ID NO: 1) or II (RXXXpSXP or SEQ ID NO: 2) of the classic 14-3-3 motifs. These motifs on all three proteins are suboptimal, varying by 1 to 2 amino acids from the classic 14-3-3 motifs. MA-10 cells were treated with 8-Br-cAMP for 0, 15, 30, 60 and 120 minutes. Cross-linking (CL) was performed with photo-activatable leucine and methionine and UV light. Cell lysates were immunoprecipitated with 14-3-3ε anti-sera (IP). Immunoblot analysis confirms the previous results (FIG. 2) and shows the dynamics of 14-3-3ε interactions with other (b) 14-3-3 isoforms (14-3-3 pan), STAR, (c) TSPO, STAR and VDAC1 during steroidogenesis, C lane indicates these interactions in native MA-10 cell protein lysates.

FIG. 13 provides the alignment of amino acid sequences of 14-3-3ε (a) and VDAC1 (b) showing high degree of conservation for both proteins and that the 14-3-3 binding motif is conserved in the three mammalian species as indicated.

DETAILED DESCRIPTION

Figure 2B:
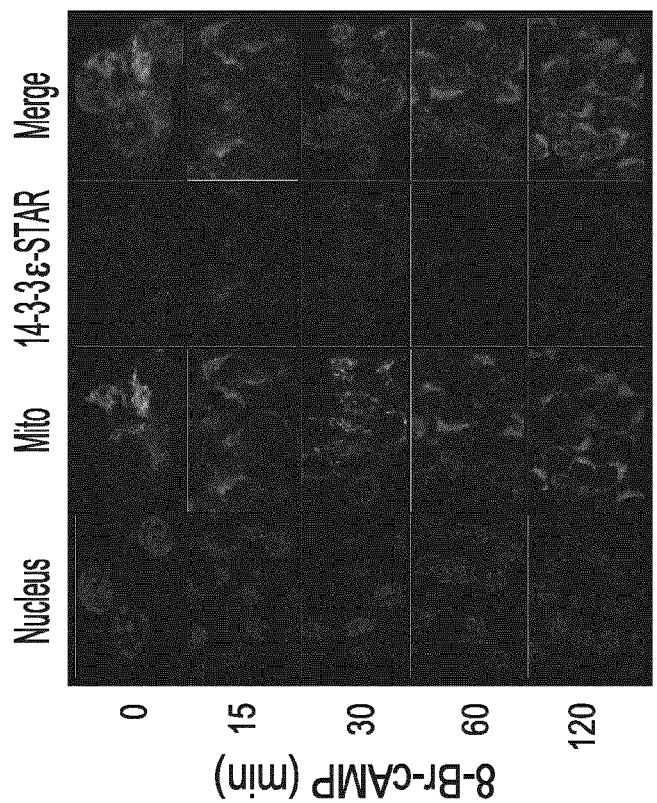
FIG. 2 illustrates that TSPO, STAR, and VDAC1 are targets of 14-3-3ε. (a, b, c, d) Cell immunoprecipitation (Duolink technology) indicates the dynamics of the interactions between 14-3-3ε with TSPO, STAR and VDAC1. Images show the cell nucleus (first column of each panel), mitochondria (second column of each panel), and endogenous protein-protein interactions (third column of each panel) between 14-3-3ε-TSPO (a), 14-3-3ε-STAR (b), and 14-3-3ε-VDAC1 (c) the background signal (d) of the Duolink assay in MA-10 cells, and the merge of the three previous columns (last column). (e, f, g) Corresponding analysis of the cell immunoprecipitation assays shown in FIGS. 2a to 2c for the 14-3-3ε-TSPO interaction (e), the 14-3-3ε-STAR interaction (f) or the 14-3-3ε-VDAC1 interaction (g). Results are shown as the signal of the interacting proteins per cell in function of time of incubation with 8-Br-cAMP (in minutes). * P<0.05) and *** P<0.001.

Throughout this application, various terms are used and some of them are more precisely defined herein.

14-3-3ε protein. As used in the context of the present disclosure, the 14-3-3ε protein is encoded by the YWHAE gene and is an adapter protein involved in the regulation of a large spectrum of both general and specialized signaling pathways. The 14-3-3ε protein binds to a large number of partners, usually by recognition of a phosphoserine or phosphothreonine motif. In the context of the present disclosure, the 14-3-3ε protein has been shown to interact with the VDAC1 protein and such interaction modulates (e.g. decreases) endogenous steroid production, such as endogenous testosterone protein. As shown herein, particularly in FIG. 13a, the 14-3-3ε protein is largely conserved amongst mammals. The 14-3-3ε protein has been documented in humans (Accession Number P62258), in mouse (Accession Number P62259) as well as in rats (Accession P62260). In some embodiments, the 14-3-3ε protein comprises or consists of the consensus sequence shown in FIG. 13a or any one of the sequences presented set forth in SEQ ID NO: 17, 18 or 19.

Antagonist. This term, as used herein, refers to an agent that impedes or decreases the formation and/or stability of an hetero-complex between the 14-3-3ε protein and the VDAC1 protein. An antagonist can also be a compound which decreases the stability of a 14-3-3ε/VDAC1 complex, which downregulates the expression of a 14-3-3ε-encoding gene, which limits the expression of a 14-3-3ε-encoding transcript (e.g., mRNA), which dowregulates the expression of a VDAC1-encoding gene, which limits the expression of a VDAC1-encoding transcript (e.g., mRNA), which favors the degradation of the 14-3-3ε polypeptide and/or which favors the degradation of the VDAC1 polypeptide. In the context of this disclosure, such antagonists are considered useful for the prevention, treatment and/or alleviation of symptoms of conditions associated with hypogonadism.

Conditions associated with hypogonadism. Hypogonadism is understood as diminished functional activity of the gonads (e.g., the testes and ovaries) resulting in diminished sex hormone (e.g., testosterone, estradiol, biosynthesis progesterone, DHEA, anti-Müllerian hormone, activin and inhibin). Low androgen (e.g., testosterone) levels can be referred to as hypoandrogenism and low estrogen (e.g., estradiol) can be referred to as hypoestrogenism. Conditions associated with hypogonadism include, but are not limited to infertility (due to defective or insufficient spermatogenesis or ovulation), aging, decreased libido, sexual dysfunction, altered mood, fatigue, decreased lean body mass, decreased bone mineral density, increased visceral fat and metabolic syndrome.

Pharmaceutically effective amount or therapeutically effective amount. These expressions refer to an amount (dose) effective in mediating a therapeutic benefit to a subject (for example prevention, treatment and/or alleviation of symptoms a condition associated with hypogonadism). The pharmaceutically effective amount can be used in relationship to the antagonist as described herein. It is also to be understood herein that a "pharmaceutically effective amount" may be interpreted as an amount giving a desired therapeutic effect, either taken in one dose or in any dosage or route, taken alone or in combination with other therapeutic agents.

Prevention, treatment and alleviation of symptoms. These expressions refer to the ability of a method or an agent to limit the development, progression and/or symptomology of a condition associated with hypogonadism. Broadly, the prevention, treatment and/or alleviation of symptoms encompass the of reduction of symptoms associated with hypogonadism, such as, for example, infertility (due to defective or insufficient spermatogenesis or ovulation), aging, decreased libido, sexual dysfunction, altered mood, fatigue, decreased lean body mass, decreased bone mineral density, increased visceral fat and metabolic syndrome.

Reaction vessel. The reaction vessel is an in vivo or in vitro discrete unit for characterizing a potential therapeutic agent. When a potential therapeutic agent is being screened, the contact between the agent, the 14-3-3ε protein and the VDAC1 protein must be made under conditions suitable and for a period of time sufficient to allow, when possible, interactions between the agent the 14-3-3ε protein and the VDAC1 protein. Suitable in vitro environments can include, for example, a cell-free environment is combined in a reaction media comprising the appropriate reagents to enable the various measurements. Other suitable in vitro environments include cell-based assays (comprising, for example, using testis cells such as Leydig cells) or tissue-based assays (for example using isolated testis).

RNA interference. RNAi is a post-transcriptional gene silencing process that is induced by a miRNA or a dsRNA (a small interfering RNA; siRNA) and has been used to modulate gene expression. Generally, RNAi is being performed by contacting cells with a double stranded siRNA ou a small hairpin RNA (shRNA). However, manipulation of RNA outside of cells is tedious due to the sensitivity of RNA to degradation. It is thus also encompassed herein a deoxyribonucleic acid (DNA) compositions encoding small interfering RNA (siRNA) molecules, or intermediate siRNA molecules (such as shRNA), comprising one strand of an siRNA. Accordingly, the present disclosure provides an isolated DNA molecule, which includes an expressible template nucleotide sequence encoding an intermediate siRNA, which, when a component of an siRNA, mediates RNA interference (RNAi) of a target RNA (e.g., a mRNA or transcript encoding the 14-3-3ε protein). The suppression of gene expression caused by RNAi may be transient or it may be more stable, even permanent.

VDAC1 protein. As used in the context of the present disclosure, the VDAC1 protein, also known as voltage-dependent anion-selective channel protein 1, is encoded by the VDAC1 gene and forms a channel through the mitochondrial outer membrane and the plasma membrane. As shown herein, the VDAC1 protein can interact with the TSPO protein to form a mitochondrial channel for the transport of cholesterol. As also shown herein, the VDAC1 protein comprises 14-3-3ε binding motifs (e.g., KTKSEN (SEQ ID NO: 13) and RVTQSNF (SEQ ID NO: 14) as shown in FIG. 8a) and is capable of binding to the 14-3-3ε protein. Such interaction between the VDAC1 protein and the 14-3-3ε protein has been shown to modulate (e.g., decrease) endogenous steroid production, particularly endogenous testosterone protein. As also shown herein, and particularly in FIG. 13b, the VDAC1 protein is largely conserved amongst mammals. It has been documented in humans (Accession Number NP_003365), in mouse (Accession Number NP_035824) as well as in rats (Accession NP_112643). In some embodiments, the VDAC1 protein comprises or consists of the consensus sequence shown in FIG. 13b or any one of the sequences presented set forth in SEQ ID NO: 20, 21 or 22. It is worth noting that the serine residue located at position 167 of the VDAC1 protein sequence (as shown in any one of SEQ ID NO: 20 to 22 and which corresponds to the serine residue in RVTQSNF (SEQ ID NO: 5)) is involved in the association between the 14-3-3ε protein and the VDAC1 protein.

Agents for Promoting Endogenous Steroidogenesis Production

The present disclosure provides novel peptides comprising a 14-3-3ε binding motif, peptidomimetics of such peptides as well as chimeric peptides comprising such peptides. As it will be shown herein, these peptides are capable of limiting the interaction between the 14-3-3ε protein and the VDAC1 protein and ultimately favor the endogenous steroidogenesis (in vitro or in vivo), particularly the production of testosterone.

In an embodiment, the peptides described herein are capable of binding to the 14-3-3ε protein, and in an embodiment, are capable of binding to the 14-3-3ε protein in a region (or in the vicinity of the region) where the STAR and/or the VDAC1 protein binds to the 14-3-3ε protein. In a further embodiment, the peptides are capable of limiting or inhibiting the binding of the STAR and/or the VDAC1 protein to the 14-3-3ε protein. In some embodiments, the peptides are derived from a mouse VDAC1 protein (SEQ ID NO: 20) and possesses a serine residue at a location corresponding to 167 in the mature mouse VDAC1 protein which corresponds to a serine residue at a location corresponding to 180 of the immature mouse VDAC1 protein (e.g., whose transcript has not been spliced). This serine residue is conserved in the human VDAC1 protein (e.g., residue located at position 167 of SEQ ID NO: 21) as well as in the rat VDAC protein (e.g., residue located at position 167 SEQ ID NO: 22). In an embodiment, the peptide is derived from the mouse VDAC1 species and corresponds to the amino acid residues located between positions 163 and 169 of SEQ ID NO: 20. In another embodiment, the peptide is derived from a human VDAC1 species and corresponds to the amino acid residues located between positions 163 and 169 of SEQ ID NO: 21. In still another embodiments, the peptide is derived from a rat VDAC1 species and corresponds to the amino acid residues located between positions 163 and 169 of SEQ ID NO: 22. In yet another embodiment, the peptide can be chemically synthesized to have or consist of the following amino acid sequence RVTQSNF (SEQ ID NO: 5).

Particularly advantageous peptides are those having or consisting of the amino acid sequence RVTQSNF (SEQ ID NO: 5) as well as peptidomimetic versions thereof. As shown herein, the peptide having or consisting of the amino acid sequence RVTQSNF (SEQ ID NO: 5) is capable of limiting or impeding the physical association between the 14-3-3ε protein and the VDAC1 protein which in return allows endogenous steroid production (such as testosterone production) without modulating the production of the luteinizing hormone. As also shown herein, the serine residue of the RVTQSNF (SEQ ID NO: 5) is important for such biological activity since the replacement of such serine residue (by a glycine residue for example) abrogates the peptide's ability to upregulate endogenous steroid production. In an embodiment, the peptide can have or consist of the amino acid sequence of SKSRVTQSNFAVG (SEQ ID NO: 30). As also shown herein, the serine residue at position 8 of SEQ ID NO: 30 is important for such biological activity since the replacement of such serine residue (by a glycine residue for example) abrogates the peptide's ability to upregulate endogenous steroid production. In some embodiments, the peptide can be phosphorylated at least at one amino acid residue. For example, the peptide can be phosphorylated at the serine residue located at position 5 of the amino acid sequence RVTQSNF (SEQ ID NO: 5) or at position 8 of the amino acid sequence SKSRVTQSNFAVG (SEQ ID NO: 30). The presence of a phosphorylated serine residue on the peptide can, in some embodiments, increases the affinity of the peptide for the 14-3-3ε protein and ultimately further enhance or prolong endogenous steroid production. In an embodiment, the isolated peptide is at least 7, 8, 9, 10, 11, 12 or 13 amino acid long. In yet another embodiment, the isolated peptide is no more than 13, 12, 11, 10, 9, 8 or 7 amino acid long.

The present disclosure also provides a chimeric peptide (as well as corresponding peptidomimetic versions thereof) having or consisting of the peptide described herein (which may or may not be phosphorylated) fused to a cell penetrating peptide. As used herein, the term "cell penetrating peptide" refers to a peptide capable of enhancing penetration across certain cellular structures, such as the cytoplasmic membrane, the mitochondrial membrane or the nuclear membrane. Some penetrating peptides can be specific or derived from a protein transduction domain. Other penetrating peptide can be specific or derived from a growth factor or a hormone. An exemplary targeting/penetrating peptide can be a blood-brain-barrier (BBB)-permeant, amyloid-targeting/penetrating peptide such as KKLVFFAξGC or a cell penetrating fragment thereof (as presented in U.S. Pat. No. 7,803,351). Another exemplary penetrating peptides include, but are not limited to, the TAT protein or a cell penetrating fragment thereof (such as, for example YGRKKRRQRRR (SEQ ID NO: 29). A further exemplary penetrating peptide is antenapedia or a cell-penetrating fragment thereof. In an embodiment, the cell penetrating peptide of the chimeric peptide is at least 5, 6, 7, 8, 9, 10 or 11 amino acid long. In still another embodiment, the cell penetrating peptide of the chimeric peptide is no more than 11, 10, 9, 8, 7, 6 or 5 amino acid long.

In the chimeric peptides described herein, the isolated peptide and the cell penetrating peptide can be directly fused (e.g., linked) to one another. However, in another embodiment, the isolated peptide can be indirectly fused (e.g., linked) to the cell penetrating peptide via a linker (such as an amino acid linker, a glycine linker for example). The linker can be, for example, at least 1, 2, 3, 4 or 5 amino acid long.

In an embodiment of the chimeric peptide described herein, the carboxy terminus of the cell penetrating peptide is fused to the amino terminus of the isolated peptide. The amino acid sequence of an exemplary chimeric peptide is provided at SEQ ID NO: 7. In such chimeric peptide, the carboxy terminus of a TAT protein was fused to a linker (e.g., a single glycine residue). The carboxy terminus of the linker was fused to a peptide comprising the 14-3-3ε binding motif SKSRVTQSNFAVG (SEQ ID NO: 30). Such chimeric peptide was shown to alter the formation of a complex between the 14-3-3ε protein and the VDAC1 as well as to increase steroid production ex vivo and in vivo. The chimeric peptide can also be phosphorylated at a single amino acid residue or at a plurality of amino acid residues. In the embodiment of the chimeric peptide presented in SEQ ID NO: 7, the serine residue at position 20 can be phosphorylated. The chimeric peptide can be made using recombinant expression in a transgenic host or can be synthetically synthesized.

The present disclosure also provides a delivery system comprising the isolated peptide described herein or the chimeric peptide (as well as peptidomimetic version of such peptide or chimeric peptide) described herein and a cell penetration enhancer. As used herein, a "cell penetration enhancer", when complexed with the isolated peptide or the chimeric peptide, facilitates the passage of the peptide across a cellular structure or a cellular membrane (such as the cytoplasmic membrane, the mitochondrial membrane or the nuclear membrane for example). Exemplary embodiments of the delivery system include, but are not limited to, viral delivery systems, nanoparticles and liposomes.

The present disclosure also provides nucleic acid molecules (e.g., encoding siRNAs) capable of impeding the expression of the 14-3-3ε protein which, in some conditions, can be useful for promoting endogenous production of a steroid (such as testosterone for example). In the context of the present disclosure, siRNA are double stranded RNA molecules from about 10 to about 30 nucleotides (for example between 12 to 28 nucleotides long, more preferably 13 to 20 nucleotides long, even more preferably 16 to 19 nucleotides long) recognized for their ability to specifically interfere with the expression of the 14-3-3ε protein. In one embodiment, siRNAs of the present disclosure are 12, 13, 14, 15, 16, 17, 18, 19, 20, 21, 22, 23, 24, 25, 26, 27 or 28 nucleotides in length. As used herein, siRNA molecules need not to be limited to those molecules containing only RNA, but further encompass chemically modified nucleotides and non-nucleotides. An siRNA molecule can be assembled from two nucleic acid fragments wherein one fragment comprises the sense region and the second fragment comprises the antisense region of siRNA molecule (such as, for example, the siRNA sequences presented in Table 2). The sense region and antisense region can also be covalently connected via a linker molecule. The linker molecule can be a polynucleotide linker or a non-polynucleotide linker. Exemplary siRNA pairs include, but are not limited to the siRNAs having or consisting of the nucleic acid sequence of SEQ ID NO: 23 and 24, the siRNAs having or consisting of the nucleic acid sequence of SEQ ID NO: 25 and 26 or the siRNAs having or consisting of the nucleic acid sequence of SEQ ID NO: 27 or 29.

Therapeutic Applications

As shown herein, disrupting the formation of a complex between the 14-3-3ε protein and the VDAC1 protein, for example by using a 14-3-3ε antagonist, can be useful in promoting endogenous steroid production. As also shown herein, the TSPO-VDAC complex facilitates the import of cholesterol in mitochondria, which is a rate-limiting step in steroid biosynthesis. Without wishing to be bound to theory, it is assumed that by inhibiting the formation of a complex between the 14-3-3ε protein and the VDAC1 protein, the latter has increased availability to form a complex with TSPO to ultimately increase the import of cholesterol in mitochondria. As such, the expression of all steroid formed from cholesterol could be affected (e.g., increased) by modulating the interaction between the 14-3-3ε protein and the VDAC1 protein. Because the isolated peptide and chimeric peptides (optionally presented in a delivery system) as well as the nucleic acid molecules described herein have the ability to promote the endogenous production of a steroid, they can be advantageously used to modulate levels of steroid production in a cell, in an organism and in some embodiments, in therapy. For example, in a therapeutic application, the isolated peptide, the chimeric peptide (optionally presented in a delivery system) or the nucleic acid molecule (or combination thereof) is contacted with a cell (either in vitro or in vivo) under conditions suitable for promoting the endogenous production of the steroid (such as, for example, testosterone).

In therapeutic applications, the isolated peptide, the chimeric peptide, the delivery system or the nucleic acid molecule can optionally be formulated in a pharmaceutical composition with a pharmaceutically acceptable excipient. Further, the isolated peptide, the chimeric peptide, the delivery system or the nucleic acid molecule can optionally be formulated for being administered as a topical composition designed to be applied on the skin, such as a cream or a gel. In addition, the isolated peptide, the chimeric peptide, the delivery system or the nucleic acid molecule can optionally be formulated for being administered as an injection either for subcutaneous, intravenous, intramuscular or intratesticular administration.

The therapeutic applications described herein can be applied to increase or stimulate the production of any metabolite of the substrate cholesterol in the pathway of steroid biosynthesis. In an embodiment of the therapeutic applications described herein, the steroid can be pregnenolone, progesterone, testosterone or other steroids formed from the substrate cholesterol during steroid biosynthesis. Evidently, testosterone formation involves pregnenolone, progesterone, 17-hydroxyprogestreone and the end product testosterone which could further be metabolized to estradiol. In the female, the end products could be progesterone and estrogen. Furthermore, since the mechanism of action described herein relates to steroidogenesis in general, a further application can be made to induce neurosteroid formation (pregnenolone and progesterone metabolites for example). As such, in an embodiment, the steroid can be a neurosteroid.

In an embodiment, the therapeutic applications comprise promoting endogenous steroid production in a subject in need thereof (for example, a subject having a low steroid level or a declining steroid level). Broadly, the method comprises contacting an agent capable of impeding the formation and/or stability of an intracellular complex between a 14-3-3ε protein and a VDAC1 protein (e.g., a 14-3-3ε protein antagonist) so as to promote endogenous steroid production. In an embodiment, the therapeutic agent is capable of limiting or inhibiting the expression of the 14-3-3ε protein. Such agent include, but is not limited to, a siRNA or a combination of siRNAs capable of specifically inhibiting the expression of transcripts encoding the 14-3-3ε protein (such as, for example, the triple combinations of siRNA described below). Alternatively, the therapeutic agent is capable of limiting or inhibiting the interaction between the 14-3-3ε protein and the VDAC1 protein. For example, such therapeutic agent includes, but is not limited to, the isolated peptide described herein, the chimeric described herein or the delivery system described herein.

In addition, in the therapeutic applications described herein, the treated cell can be in vitro or in vivo. In the latter embodiment, the method can comprise administering the isolated peptide, the chimeric peptide, the delivery system or the nucleic acid molecule to a subject in need thereof. The isolated peptide, the chimeric peptide, the delivery system or the nucleic acid molecule is administered at a therapeutic effective amount to achieve the desired results.

In the therapeutic applications described herein, the subject can be a mammal and, in a further embodiment, a male. In an embodiment, the male is at least 30 years old or, in a further embodiment, at least 50 years old. Testosterone production in the males declines after the age of 30 years old and there is annual decline of 1-20 in total testosterone levels. Thus, testosterone replacement therapy (in this case induction of endogenous T production) could be applicable at any time when testosterone decline begins and/or the symptoms associated with testosterone decline (low libido and erection, low lean mass, reduced energy, central adiposity, lack of coping with stressors, etc. are indicative of testosterone decline). These symptoms are more prominent with aging and are more commonly seen in men over 50 where the cardiovascular disease, metabolic syndrome and depression are added in the list of the phenotypes associated with testosterone decline. Moreover, even at ages younger than 30 years old, the use of the therapeutic agent described herein could assist in cases of male infertility due to hypogonadism.

In the therapeutic applications described herein, the treated cell can be from or located in a testis and, in a further embodiment, the treated cell can be a Leydig cell. In another embodiment, the cell can be from or located in an ovary, an adrenal gland and/or a brain.

The therapeutic applications described herein can be used for the prevention, treatment and/or alleviation of symptoms of a condition associated with a decline in a steroid level. One exemplary condition associated to a decline in a steroid level is hypogonadism. Such conditions include, but are not limited to infertility, subfertility, aging, decreased libido, sexual dysfunction, altered mood, fatigue, decreased lean body mass, decreased bone mineral density, increased visceral fat, metabolic syndrome.

The therapeutic applications described herein can be used for the prevention, treatment and/or alleviation of symptoms associated with a condition associated to a decline in steroid levels, for example, a decline in neurosteroid levels. Such conditions include, but are not limited to anxiety disorders and depression.

In an embodiment, the therapeutic applications described herein can be used for the prevention, treatment and/or alleviation of symptoms associated with a condition associated to a decline in steroid levels. Such conditions include, but are not limited to, depression, organ failure, cardiac muscle stiffness, low energy, hematocrit, and coping with stressors.

In some embodiments, the isolated peptides and chimeric peptides provided herewith can penetrate cell membranes easily with high transfection efficiency and within a short period of time. In alternate embodiments, the isolated peptides and chimeric peptides are active in vitro and in vivo in inducing steroid formation by testicular Leydig cells. In another embodiment, the isolated peptides and chimeric peptides can induce endogenous T levels in a manner comparable to that induced by the gonadotropin luteinizing hormone (LH).

Administration is by any of the routes normally used for introducing the therapeutic agents into ultimate contact with circulation (blood or cerebrospinal fluid for example) or tissue cells. The therapeutic agents described herein can be administered in any suitable manner, preferably with the pharmaceutically acceptable carriers or excipients. The terms "pharmaceutically acceptable carrier", "excipients" and "adjuvant" and "physiologically acceptable vehicle" and the like are to be understood as referring to an acceptable carrier or adjuvant that may be administered to a patient, together with a compound of this disclosure, and which does not destroy the pharmacological activity thereof. Further, as used herein "pharmaceutically acceptable carrier" or "pharmaceutical carrier" are known in the art and include, but are not limited to, 0.01-0.1 M and preferably 0.05 M phosphate buffer or 0.8% saline. Additionally, such pharmaceutically acceptable carriers may be aqueous or non-aqueous solutions, suspensions, and emulsions. Examples of non-aqueous solvents are propylene glycol, polyethylene glycol, vegetable oils such as olive oil, and injectable organic esters such as ethyl oleate. Aqueous carriers include water, alcoholic/aqueous solutions, emulsions or suspensions, including saline and buffered media. Parenteral vehicles include sodium chloride solution, Ringer's dextrose, dextrose and sodium chloride, lactated Ringer's or fixed oils. Intravenous vehicles include fluid and nutrient replenishers, electrolyte replenishers such as those based on Ringer's dextrose, and the like. Preservatives and other additives may also be present, such as, for example, antimicrobials, antioxidants, collating agents, inert gases and the like.

As used herein, "pharmaceutical composition" means therapeutically effective amounts (dose) of the agent together with pharmaceutically acceptable diluents, preservatives, solubilizers, emulsifiers, adjuvants and/or carriers.

A "therapeutically effective amount" as used herein refers to that amount which provides a therapeutic effect for a given condition and administration regimen. Such compositions are liquids or lyophilized or otherwise dried formulations and include diluents of various buffer content (e.g., Tris-HCl, acetate, phosphate), pH and ionic strength, additives such as albumin or gelatin to prevent absorption to surfaces, and detergents (e.g., Tween 20™, Tween 80™, Pluronic F68™, bile acid salts). The pharmaceutical composition can comprise pharmaceutically acceptable solubilizing agents (e.g., glycerol, polyethylene glycerol), anti-oxidants (e.g., ascorbic acid, sodium metabisulfite), preservatives (e.g., thimerosal, benzyl alcohol, parabens), bulking substances or tonicity modifiers (e.g., lactose, mannitol), covalent attachment of polymers such as polyethylene glycol to the protein, complexation with metal ions, or incorporation of the material into or onto particulate preparations of polymeric compounds such as polylactic acid, polyglycolic acid, hydrogels, etc., or onto liposomes, microemulsions, micelles, unilamellar or multilamellar vesicles, erythrocyte ghosts, or spheroplasts. Such compositions will influence the physical state, solubility, stability, rate of in vivo release, and rate of in vivo clearance. Controlled or sustained release compositions include formulation in lipophilic depots (e.g., fatty acids, waxes, oils). Also comprehended by the disclosure are particulate compositions coated with polymers (e.g., poloxamers or poloxamines).

Suitable methods of administering such nucleic acid molecules are available and well known to those of skill in the art, and, although more than one route can be used to administer a particular composition, a particular route can often provide a more immediate and more effective reaction than another route.

The therapeutic agents of the present disclosure may be administered, either orally or parenterally, systemically or locally. For example, intravenous injection such as drip infusion, intramuscular injection, intervertebral injection, intraperitoneal injection, intratesticular, subcutaneous injection, suppositories, intestinal lavage, oral enteric coated tablets, and the like can be selected, and the method of administration may be chosen, as appropriate, depending on the age and the conditions of the patient. The effective dosage is chosen from the range of 0.01 mg to 100 mg per kg of body weight per administration. Alternatively, the dosage in the range of 1 to 1000 mg, preferably 5 to 50 mg per patient may be chosen.

Screening Applications

A mechanism of action of the 14-3-3ε protein is provided herewith and suggests that disrupting the interaction between 14-3-3ε and VDAC1 negates the negative effects on 14-3-3ε on endogenous steroid production. As such, the present disclosure provides a screening assay for identify potential therapeutic agents for promoting endogenous steroid production. The screening method allows the determination of the usefulness of a putative agent for the promotion of endogenous steroid production. Broadly, the method comprises combining the agent with a 14-3-3ε protein and a VDAC1 protein, determining if the agent promotes or impedes the formation and/or stability of a complex between the 14-3-3ε protein and the VDAC1 protein and characterizing the agent based on this determination. If the agent impedes the formation and/or stability of the complex between the 14-3-3ε protein and the VDAC1 protein, then the agent is characterized as being useful for promoting endogenous steroid production. On the other hand, if the agent promotes the formation and/or stability of the complex between the 14-3-3ε protein and the VDAC1 protein, then the agent is characterized as lacking utility to promote endogenous steroid production.

In the screening methods described herein, the steroid can be pregnenolone, progesterone, testosterone or other steroids formed from the substrate cholesterol during steroid biosynthesis, such as a neurosteroid for example.

In the screening methods described herein, the combining step can occur in cell (either in vitro or ex vivo). The cell can be derived from a testis (such as the MA-10 cell) and/or be a Leydig cell. Alternatively, the cell can be derived from an ovary, an adrenal or a brain. The cell can be in a tissue-like state, for example from an ex vivo isolated testis. Alternatively, the combining step can be conducted in an non-human animal (a rodent for example).

The screening methods described herein are useful to identify agents for the prevention, treatment and/or alleviation of symptoms of a condition associated with hypogonadism (for example infertility, subfertility, aging, decreased libido, sexual dysfunction, altered mood, fatigue, decreased lean body mass, decreased bone mineral density, increased visceral fat and/or metabolic syndrome).

In order to determine if an agent would be useful for preventing hypogonadism, an agent to be screened is contacted with uncomplexed (e.g., free) 14-3-3ε proteins and VDAC1 proteins. In order to determine if an agent would be useful for treating and/or alleviating the symptoms of hypogonadism, the 14-3-3ε protein and the VDAC1 protein are first contacted and allowed to interact to form a complex and then an agent to be screened is added. This contact may occur by placing the agent, the 14-3-3ε protein and the VDAC1 protein in a reaction vessel. In the assays, the reaction vessel can be any type of container that can accommodate the measurement of a parameter of the complex between the 14-3-3ε protein and the VDAC1 protein (for example the level of formation or of dissociation of the complex and/or the stability of the complex).

For screening applications, a suitable in vitro environment for the screening assay described herewith can be a cell-free environment or a cultured cell. In an embodiment, the cultured cell should be able to maintain viability in culture. In such embodiment, the cultured cell(s) should express the 14-3-3ε protein and the VDAC1 protein. The cell is preferably derived from a steroid-producing tissue (primary cell culture or cell line) and even more preferably is a testis cell, such as a Leydig cell. If a primary cell culture is used, the cell may be isolated or in a tissue-like structure. A further suitable environment is a non-human model, such as an animal model. If the characterization of the agent occurs in a non-human model, then the model is administered with the agent. Various dosage and modes of administration may be used to fully characterize the agent's ability to prevent, treat and/or alleviate the symptoms of hypogonadism.

Once the contact has occurred, a measurement or value of a parameter of the of the complex between the 14-3-3ε protein and the VDAC1 protein is determined. This parameter can be, without limitation, the presence or the absence the complex, the rate of association of the complex and/or the rate of dissociation of the complex. This assessment may be made directly in the reaction vessel (by using a probe for example) or on a sample of such reaction vessel. Even though a single parameter is required to enable the characterization of the agent, it is also provided that more than one parameter of the complex may be measured.

The measuring step can rely on the addition of a quantifier specific to the parameter to be assessed to the reaction vessel or a sample thereof. The quantifier can specifically bind to the complex, the free 14-3-3ε protein and/or the free VDAC1 protein that is being assessed. In those instances, the amount of the quantifier that specifically bound (or that did not bind) to the complex, the 14-3-3ε protein and/or the VDAC1 protein is used to provide a measurement of the parameter of the complex.

The amount of the complex, the free 14-3-3ε protein and/or the free VDAC1 protein can be measured for example, through an antibody-based technique (such as a Western blot, an ELISA or flow cytometry), a micro-array, spectrometry, MRM mass spectrometry, etc. In one embodiment, this assay is performed utilizing antibodies specific to the complex, the free 14-3-3ε protein and/or the free VDAC1 protein. Methods for detecting such antibody-target complexes, in addition to those described above for the GST-immobilized complexes, include immunodetection of complexes, immunoprecipitation as well as enzyme-linked assays.

In some embodiments, it is also possible to evaluate the ability of screened agent to limit or inhibit the physical association of the 14-3-3ε protein to the VDAC1 protein. To identify such agents, a reaction mixture containing the 14-3-3ε protein to the VDAC1 protein is prepared, under conditions and for a time sufficient, to allow the two polypeptides to form complex. In order to test if an agent which impedes the interaction between the 14-3-3ε protein and the VDAC1 protein, the reaction mixture can be provided in the presence and absence of the test agent. The test agent can be initially included in the reaction mixture, or can be added at a time subsequent to the formation of the 14-3-3ε/VDAC1 protein complex. The formation of any complexes between the target product and the cellular or extracellular binding partner is then detected. This type of assay can be accomplished, for example, by coupling one of the components, with a label such that binding of the labeled component to the other can be determined by detecting the labeled compound in a complex. A component can be labeled with $^{125}$I, $^{35}$S, $^{14}$C, or $^{3}$H, either directly or indirectly, and the radioisotope detected by direct counting of radio-emission or by scintillation counting. Alternatively, a component can be enzymatically labeled with, for example, horseradish peroxidase, alkaline phosphatase, or luciferase, and the enzymatic label detected by determination of conversion of an appropriate substrate to product. The interaction between two molecules can also be detected, e.g., using a fluorescence assay in which at least one molecule is fluorescently labeled. One example of such an assay includes fluorescence energy transfer (FET or FRET for fluorescence resonance energy transfer). A FET binding event can be conveniently measured through standard fluorometric detection means well known in the art (e. g., using a fluorimeter). Another example of a fluorescence assay is fluorescence polarization (FP). In another embodiment, the measuring step can rely on the use of real-time Biomolecular Interaction Analysis (BIA).

In one embodiment of the screening applications, the 14-3-3ε protein or the VDAC1 protein can be associated onto a solid phase. Examples of such solid phase include microtiter plates, test tubes, array slides, beads and micro-centrifuge tubes. Following incubation, the solid phases are washed to remove any unbound components, the matrix immobilized in the case of beads, complex determined either directly or indirectly.

Alternatively, the screening assays can be conducted in a liquid phase. In such an assay, the reaction products are separated from unreacted components, by any of a number of standard techniques, including but not limited to: differential centrifugation; chromatography (gel filtration chromatography, ion-exchange chromatography) and/or electrophoresis. Such resins and chromatographic techniques are known to one skilled in the art. Further, fluorescence energy transfer may also be conveniently utilized, as described herein, to detect binding without further purification of the complex from solution.

In addition to cell-based and in vitro assay screening systems, non-human organisms, e.g. transgenic non-human organisms or a model organism, can also be used. A transgenic organism is one in which a heterologous DNA sequence is chromosomally integrated into the germ cells of the animal. A transgenic organism will also have the transgene integrated into the chromosomes of its somatic cells. Organisms of any species, including, but not limited to: yeast, worms, flies, fish, reptiles, birds, mammals (e.g. mice, rats, rabbits, guinea pigs, pigs, micro-pigs, and goats), and non-human primates (e.g. baboons, monkeys, chimpanzees) may be used in the methods described herein.

In another assay format, the specific activity or level of the 14-3-3ε protein and the VDAC1 protein complex, normalized to a standard unit, may be assayed in a cell-free system, a cell line, a cell population or animal model that has been exposed to the agent to be tested and compared to an unexposed control cell-free system, cell line, cell population or animal model.

Once the measurement has been made, it is extracted from the reaction vessel and the value of the parameter of the complex can optionally be compared to a control value. In an embodiment, the control value is associated with a lack of prevention, treatment and/or alleviation of symptoms of hypogonadism. In such assay format, agents useful in the prevention, treatment and/or alleviation of symptoms of hypogonadism are able, when compared to the control, decrease the formation or stability the complex. Still in such assay format, the agents are not considered to be useful if the agent maintain or increase the formation of the complex.

In another embodiment, the control value is associated with the prevention, treatment and/or alleviation of symptoms of hypogonadism. In such assay format, agents useful in the prevention, treatment and/or alleviation of symptoms of hypogonadism are, when compared to the control, able to maintain or decrease the formation of the complex. Still in such assay format, the agents are considered not to be useful if the agent increases or favors the formation the complex.

In the screening methods, the control value may be the parameter of the complex in the absence of the agent. In this particular embodiment, the parameter of the complex can be measured prior to the combination of the agent with the complex or in two replicates of the same reaction vessel where one of the screening system does not comprise the agent. The control value can also be the parameter of the complex in the presence of a control agent that is known not to prevent/treat/alleviate the symptoms of hypogonadism. Such control agent may be, for example, a pharmaceutically inert excipient. The control value can also be the parameter of complex obtained from a reaction vessel comprising cells or tissues from a healthy subject (e.g., age- and sex-matched) that is not afflicted by hypogonadism.

The comparison can be made by a subject or in a comparison module. Such comparison module may comprise a processor and a memory card to perform an application. The processor may access the memory to retrieve data. The processor may be any device that can perform operations on data. Examples are a central processing unit (CPU), a front-end processor, a microprocessor, a graphics processing unit (PPU/VPU), a physics processing unit (PPU), a digital signal processor and a network processor.

The application is coupled to the processor and configured to determine the effect of the agent on the parameter of the complex with respect to the control value. An output of this comparison may be transmitted to a display device. The memory, accessible by the processor, receives and stores data, such as measured parameters of the complex or any other information generated or used. The memory may be a main memory (such as a high speed Random Access Memory or RAM) or an auxiliary storage unit (such as a hard disk, a floppy disk or a magnetic tape drive). The memory may be any other type of memory (such as a Read-Only Memory or ROM) or optical storage media (such as a videodisc or a compact disc).

Once the determination and optionally the comparison has been made, then it is possible to characterize the agent. This characterization is possible because, as shown herein, impeding the formation of the complex is associated with increased steroid production in vivo or in vitro.

The characterization can be made by a subject or with a processor and a memory card to perform an application. The processor may access the memory to retrieve data. The processor may be any device that can perform operations on data. Examples are a central processing unit (CPU), a front-end processor, a microprocessor, a graphics processing unit (PPU/VPU), a physics processing unit (PPU), a digital signal processor and a network processor. The application is coupled to the processor and configured to characterize the agent being screened. An output of this characterization may be transmitted to a display device. The memory, accessible by the processor, receives and stores data, such as measured parameters of the complex or any other information generated or used. The memory may be a main memory (such as a high speed Random Access Memory or RAM) or an auxiliary storage unit (such as a hard disk, a floppy disk or a magnetic tape drive). The memory may be any other type of memory (such as a Read-Only Memory or ROM) or optical storage media (such as a videodisc or a compact disc).

The present disclosure also provides screening systems for performing the characterizations and methods described herein. These systems comprise a reaction vessel for placing the 14-3-3ε protein and the VDAC1 protein and the and the agent, a processor in a computer system, a memory accessible by the processor and an application coupled to the processor. The application or group of applications is(are) configured for receiving a test value of a parameter of the complex in the presence of the agent; comparing the test value to a control value and/or characterizing the agent in function of this comparison.

The present disclosure also provides a software product embodied on a computer readable medium. This software product comprises instructions for characterizing the agent according to the methods described herein. The software product comprises a receiving module for receiving a test value the complex in the presence of an agent; a comparison module receiving input from the measuring module for determining if the test value is lower than, equal to or higher than a control value; a characterization module receiving input from the comparison module for performing the characterization based on the comparison.

In an embodiment, an application found in the computer system of the system is used in the comparison module. A measuring module extracts/receives information from the reaction vessel with respect to the test value of the complex. The receiving module is coupled to a comparison module which receives the value(s) of the level of the complex and determines if this value is lower than, equal to or higher than a control value. The comparison module can be coupled to a characterization module.

In another embodiment, an application found in the computer system of the system is used in the characterization module. The comparison module is coupled to the characterization module which receives the comparison and performs the characterization based on this comparison.

In a further embodiment, the receiving module, comparison module and characterization module are organized into a single discrete system. In another embodiment, each module is organized into different discrete system. In still a further embodiment, at least two modules are organized into a single discrete system.

The present invention will be more readily understood by referring to the following examples which are given to illustrate the invention rather than to limit its scope.

EXAMPLE

Cell culture, treatments, and steroid measurement. MA-10 mouse Leydig tumor cells were maintained in DMEM/Ham's nutrient mixture F12 (Gibco, Burlington, ON) supplemented with 5% fetal bovine serum, 2.5% hoarse serum, and 1% penicillin and streptomycin at 37° C. and 3.7% $CO_2$. Cells were incubated in serum-free cell culture media supplemented with 1 mM 8-Bromo-cAMP (Enzo Biosciences, Farmingdale, N.Y.) or 1.36 µM (50 ng/ml) hCG for 15, 30, 60, and 120 min or as indicated. Human NCL-H295R cells were maintained in DMEM/F12 media supplemented with 2.5% Ultroser G (Pall Biospera, Mississauga, ON), 1% penicillin/streptomycin (Invitrogen, Carlsbad, Calif.), and 1% ITS+ Premix (BD Biosciences, Franklin Lakes, N.J.) in a humidified chamber at 37° C. and 5% $CO_2$.

Experiments involving the TV peptides included $1 \times 10^3$ MA-10 or NCL-H295R cells, which were initially cultured for 24 hrs. Serum-free media were supplemented with 250 nM TV fusion peptides, and cells were incubated for 90 min after optimization. For the experiments with 19-Atriol, $1 \times 10^3$ MA-10 cells were cultured for 24 hrs. Serum-free media were supplemented with 10 µM 19-Atriol and cells were treated for 120 min (Gwynne et al. 1982).

In the siRNA transfection studies, $4 \times 10^5$ MA-10 cells were plated in gelatin-coated 100-mm cell culture dishes and incubated for 24 hrs. Cells were transfected with 5, 10, or 20 nM of a mixture of three pre-designed siRNA (IDT, San Jose, Calif.) sequences (Table 1) using Lipofectamine RNAiMAX™ (Invitrogen, Carlsbad, Calif.) and Opti-MEM™ transfection medium. DMEM/F12 culture media without antibiotics was added to reach 5 mL for the 72-h incubation period. HPRT siRNA and scrambled siRNA were transfected at 10 nM each and served as positive and negative control, respectively (IDT, San Jose, Calif.). The optimum concentration of 14-3-3ε siRNA, which was used for further studies, was 10 nM siRNA (Table 1), which achieved 55-75% K/D (Table 1).

TABLE 1

Sequences of the 14-3-3ε specific siRNA

| siRNA sequence | SEQ ID NO: |
|---|---|
| 5'-GCAAGAUCAUCAUUAGAA-3', | 23, |
| 3'-UUUCCAUUUCUAAUGAUG-5' | 24 |

TABLE 1-continued

Sequences of the 14-3-3ε specific siRNA

| siRNA sequence | SEQ ID NO: |
|---|---|
| 5'-GGGAGGAGAGGACAAAUU-3', | 25, |
| 3'-CAUCUUUAAUUUGUCCUC-5 | 26 |
| 5'-AGAUGAGAAUCAGUGAGA-3' | 27, |
| 3'-UAUUUCGUCUCACUGAUU-5' | 28 |

Progesterone or testosterone levels were measured with specific RIAs in triplicate using commercial anti-sera from rabbit and sheep, respectively (MP Biomedicals, Santa Ana, Calif.). Protein levels in MA-10 cell lysates were determined with the Bradford dye assay (Bio-Rad). LH and corticosterone levels were measured with rat-specific ELISA kits (CUSABIO, Wuhan, China).

Animals studies. Animals were handled according to protocols approved by the McGill University Animal Care and Use Committees. 60- to 64-day-old male Sprague-Dawley rats were purchased from Charles River, Senneville, QC. Rats were provided standard diets and tap water ad libitum and were maintained in controlled conditions (24° C., 12-h light, 12-h dark schedule). Animals were euthanized, and the testes were either immediately used for organ culture or intratesticular fluid collection, or testes and adrenal glands were snap-frozen for sectioning. Bolus injections with water or indicated doses of TV peptides were performed after administering isofluorane anesthesia. Rats were injected with either water or the indicated dose of TV fusion peptide. When FGIN-1-27 (Sigma-Aldrich, St. Louis, Mo.) was used, 8.5 µg in 50 µl (390 µM) of the compound in 1% DMSO solution containing Tween-20™ was injected into one of the testes of 68-72 day old Sprague-Dawley rats. Animals were incubated in standard conditions for 2 hrs. Surgeries were performed on 60- to 64-day-old rats bolus injection of water or TV peptides. Alzet mini-osmotic pumps releasing 75 ng of filled with water or a TV peptide or water over a course of 24 hrs was surgically implanted in the abdomen. The pumps were connected to a polyethylene catheter tubing (Alzet) and directed to the injected testis. The pump released 75 ng TV peptide to the testis over a course of 24 hrs at the rate of 1 µl/hour. GnRH antagonist, Cetrorelix™ (Sigma Aldrich) was injected into 59-day-old rats intraperitoneally (i.p.) at 0.4 mg/animal/day for 0-4 days (Horvath et al. 2004). Animal dissection was performed after $CO_2$ anesthesia. Cardiac puncture was used for blood collection, and further centrifugation yielded serum separation. Testes were dissected and either decapsulated for intratesticular fluid collection or snap-frozen for sectioning.

Ex Vivo Organ Culture. 60- to 64-day-old Sprague-Dawley rats were dissected. Testes were collected, weighed and decapsulated. A gentle mechanical disruption was performed, keeping the tubular structures intact. Testes were cultured in DMEM/F12 media with or without 250 nM TV peptides and incubated for 90 min with or without 1.36 µM hCG at 3.7% $CO_2$ and 34° C.

Immunocytochemistry and confocal microscopy. MA-10 cells ($2\times10^4$) were plated in 96-well glass-bottom dishes (Fluorodish) in triplicate until 60% confluent. Time-course treatments with 1 mM cAMP were undertaken. At the end of the incubations cells were fixed in 4° C. methanol for 3-5 minutes, permeabilized with 10% Triton X-100™ for 3 minutes, and blocked with 10% goat serum for 1 hour. 14-3-3ε antibody (1:50) and VDAC1 antibody (1:140, Abcam, Cambridge, UK) were added overnight at 4° C. The wells were washed the next day with 1×PBS and incubated in secondary anti-mouse IgG F(ab')₂ Fragment (Alexa Fluor 488™ Conjugate, Green) and anit-rabbit IgG F(ab')₂ Fragment (Alexa Fluor 555™ Conjugate, Red) (Cell Signaling Technology, Danver, Mass.) for one h. Cells were washed, DAPI was added for nuclear staining, and cells were maintained in ultra-pure water. Confocal microscopy was performed with an Olympus Fluoview FV1000 Laser Confocal Microscope at 100× magnification.

Immunohistochemistry. Testes and adrenal glands from adult mice were purchased from Cytochem Inc, Montreal, QC. Fluorescent staining was performed on testes and adrenal sections after fixing the tissues as previously explained (Aghazadeh et al. 2012), using 4% formaldehyde. Briefly, sections were permeabilized with 1% Triton X-100™, blocked with 10% goat serum in 1% BSA for 1 hour, and incubated with 14-3-3ε antibody (1:50) overnight at 4° C. in a humidity chamber. The following day, cells were washed in 1×PBS and incubated with and secondary anti-mouse IgG F(ab')₂ Fragment (Alexa Fluor 488™ Conjugate, Green; Invitrogen, Carlsbad, Calif.) for 1 hour. Hoechst (Enzo Biosciences, Farmingdale, N.Y.) was used for nuclear staining. Sections were maintained in one drop of mounting media (Invitrogen, Carlsbad, Calif.), and Images were captured with an Olympus inverted microscope with 20× and 40× lenses. Hematoxylin staining was performed on testes sections from 60- to 64-day-old Sprague-Dawley rats 24 hrs post pump implantation surgery. Tissues were snap-frozen and sectioned to be 4-6-µm thick (Cytochem Inc, Montreal, QC).

Immunoblot analysis. Immunoblot analysis was performed on protein lysates of MA-10 cells and testicular interstitial cells and adrenal glands from 60-day-old Sprague-Dawley rats. Briefly, for MA-10 cell lysate extraction, $6\times10^5$ cells were cultured in six-well gelatin-coated plates in triplicate for 24 hrs and treated with cAMP for a time course. Cells were washed with 1×PBS and harvested. For testicular interstitial cell lysates, testes were decapsulated, mechanically disrupted in RPMI 1640 media (Sigma-Aldrich, St. Louis, Mo.), and incubated in media containing 0.05% collagenase/dispase (Roche Diagnostics, Basel, Switzerland), 0.005% soybean trypsin inhibitor, and 0.001% deoxyribonuclease I (Sigma-Aldrich, St. Louis, Mo.) for 20 min at 34° C. The supernatant was collected, filtered, and centrifuged at 900 rpm for 10 min at 25° C. The Leydig-cell-enriched pellet was snap-frozen until further use. Adrenal glands were snap-frozen for later use. MA-10 cell pellets, interstitial cells, and adrenal glands were mechanically homogenized in RIPA™ lysis buffer (Cell Signaling Technology, Danver, Mass.), and protein levels were measured by the Bradford protein assay (Bio-Rad). MA-10 protein lysate (10 µg) and interstitial or adrenal protein lysates (15 µg) were solubilized and immunoblot was performed as previously described (Aghazadeh et al. 2012).

In silico prediction of the presence of the 14-3-3 binding motif. The presence of the following types of 14-3-3 binding motifs were assessed manually in Mus musculus VDAC1, TSPO, and STAR: mode I, RSXpSXP (SEQ ID NO: 1); mode II: RXXXpSXP (SEQ ID NO: 2), in which R is Arginine, S is serine, X is any amino acid, P is proline, and T is threonine; mode III: pS/pTX1-2-$CO_2H$, in which X is not proline (Yaffe et al. 1997).

Cross-linking studies. MA-10 cells (1×10⁶) were plated in gelatin-coated 100-mm Petri cell culture dishes overnight. Media were replaced with Dulbecco's Modified Eagle's Limiting Media supplemented with 10% FBS and $10^5$ mg/L photo-leucine and 30 mg/L photo-methionine (Thermo Scientific, Waltham, Mass.). Cells were incubated for 22 hrs followed by cAMP time-course treatment. Cross-linking was performed immediately after each time point with a 3UV lamp (UVP) for 16 min at 365 nm at a distance of 1 cm from the surface of the Petri dishes.

Co-immunoprecipitation. Co-immunoprecipitation was performed with Dynabeads™ Co-Immunoprecipitation Kit (Invitrogen, Carlsbad, Calif.). The 14-3-3ε specific antibody (Gegenbauer et al. 2012) was coupled with the Dynabeads™, yielding 10 mg/mL of antibody-coupled beads according to the manufacturer's instructions. Cross-linked MA-10 protein lysates were harvested in extraction buffer A (1× immunoprecipitation buffer, 1 M NaCl, and protease inhibitor without EDTA), and 0.15 mg or 0.5 mg protein was precipitated with 14-3-3ε antibody-coupled beads rotating at 4° C. for 1 hr to study 14-3-3ε dimerization or target binding, respectively. The precipitated samples were loaded onto 4-20% Tris-glycine gels. MA-10 cell lysate (10 µg) was used as a control. Immunoblotting was performed as previously described with the following antibodies: anti-14-3-3 pan (1:1000, Santa Cruz Biotechnology, Santa Cruz, Calif.), anti-TSPO (1:1000 dilution (Trott et al. 2010)), anti-STAR (1:5000 dilution (Ritchie et al. 2010)), and anti-VDAC1 (2 µg/mL, Abcam, Cambridge, UK).

In cell IP and confocal microscopy. Duolink™ technology was used (Fredriksson et al. 2002) for in cell IP. In this assay, primary antibodies raised in different species were incubated with cells or tissue sections of interest. Species-specific secondary antibodies were conjugated to short oligonucleotide tails, which form a circular oligonucleotide strand upon addition of a ligase. A polymerase was added to amplify this nucleotide strand followed by addition of a fluorescent tag, which hybridizes with this strand. Fluorescent signals were captured by confocal microscopy and measured with 0-link software. MA-10 cells were cultured at 1×10³ per well, in a 96-well glass-bottom dish (Fluorodish, Sarasota, Fla.) in triplicate and incubated overnight. The next day, cells were treated with cAMP and immediately fixed after each time point in 3.7% formaldehyde for 15 min. Sections of adult rat testes were obtained and fixed in 3.7% formaldehyde for 20 min. Fixed MA-10 cells and sections of rat testes were washed and permeabilized with 1% Triton X-100™ for one minute. Duolink™ II Red Starter Kit (OLink Biosciences, Uppsala, Sweden) was used according to the manufacturer's instructions. MA-10 cells were incubated with a combination of mouse anti-14-3-3ε (1:150) and either rabbit anti-STAR (1:150), rabbit anti-TSPO (1:150), or rabbit anti-VDAC1 (1:140) or with a different combination of rabbit anti-TSPO and mouse anti-VDAC1 (1:140) overnight at 4° C. A combination of mouse anti-14-3-3ε and rabbit anti-VDAC1 was used for rat tissue sections. Mitochondria and nuclei were stained with Mito-ID and Hoechst, respectively (Enzo Biosciences, Farmingdale, N.Y.) for 30 min at 37° C. MA-10 cells were maintained in Ultra-pure water, and tissue sections were maintained in one drop of mounting media. Protein-protein interactions were detected with Olympus Fluoview™ FV1000 Laser Confocal Microscope at 100× magnification. Z-stacks were captured from the bottom to the top of MA-10 cell nuclei. The sum of signals from all Z-stacks were measured with 0-link software and divided by the number of cells in the corresponding image to obtain the signal/cell ratio for a minimum of 60 cells. One image of each of the rat sections was captured from the middle of the nucleus, which is the area of maximum focus with the 100× lens.

Radioligand binding assays. Binding of [³H]-PK 11195 to 5 mg MA-10 cell homogenate was performed as described previously (Kramer et al. 1997). Specific [³H]-PK 11195 binding was analyzed with the iterative nonlinear curve-fitting program in GraphPad Prism 5™.

TV peptide design and labeling. TV Peptides were designed with an 11-mer of the HIV-1 virus trans-activator of transcription protein (TAT) (Nagahara et al. 1998) followed by a glycine residue and amino acids 28-40 (containing 14-3-3 motif KTKSEN (SEQ ID NO: 4)) or amino acids 160-172 (containing 14-3-3 motif RVTQSNF (SEQ ID NO: 5)) of mVDAC1. Serine residues in 14-3-3 motifs are important for 14-3-3 binding. Thus, peptides were named according to the serine residue in the peptide. TAT-VDAC1 fusion peptide S35 was named TVS35 (SEQ ID NO: 6), and TAT-VDAC1 fusion peptide S167 was named TVS167 (SEQ ID NO: 7). S35 and S167 were mutated to glycine residues as controls, and TVG35 (SEQ ID NO: 8) and TVG167 (SEQ ID NO: 9) were synthesized. TVS167 was labeled with 6-fluorescein (FAM) 488. Peptide synthesis and labeling were outperformed at the Sheldon Biotechnology Center, McGill University, Montreal, QC. Peptide sequences are shown in Table 2.

TABLE 2

Sequence of TV fusion peptides.

| Peptide Name | Sequence | 14-3-3 motif (aa #) |
|---|---|---|
| TVS35 | YGRKKRRQRRR-G-KLDLKTK<u>S</u>ENGLE (SEQ ID NO: 6) | KTKSEN (32-37) (SEQ ID NO: 4) |
| TVS35G | YGRKKRRQRRR-G-KLDLKTKGENGLE (SEQ ID NO: 8) | N. A. |
| TVS167 | YGRKKRRQRRR-G-SKSRVTQ<u>S</u>NFAVG (SEQ ID NO: 7) | RVTQSNF (163-169) (SEQ ID NO: 5) |
| TVS167G | YGRKKRRQRRR-G-SKSRVTQGNFAVG (SEQ ID NO: 9) | N. A. |

The table provides the name of the TAT-VDAC1 chimeric peptides.
The amino acid sequence of the TV peptide and the location, on the mouse VDAC1 protein are shown.

Protein sequence alignment, homology modeling, and molecular docking. The amino acid sequences for the 14-3-3ε and VDAC1 proteins in *Mus musculus*, *Homo sapiens* and *Rattus norvegicus* were aligned using ClustalW. The selected VDAC1 14-3-3 binding motif containing S167 was conserved between these three species. Coordinates of human and mouse VDAC1 and human 14-3-3ε were from the Brookhaven Protein Database (PDB: 2JK4 and 3ε MN for VDAC1; 2BR9 for 14-3-3ε). The coordinates of the putative three-dimensional structure of mouse 14-3-3ε in the absence of ligand were predicted via an automated comparative protein modeling server (Swiss-Model, Basel, Switzerland) (http://www.expasy.ch) at the University of Geneva. The optimized mode used the coordinates of the human 14-3-3γ protein (PDB: 4E2E) as a template. The putative 3-D structures of the rat VDAC1 and 14-3-3ε proteins were predicted in a similar fashion using mouse VDAC1 (PDB: 3ε MN) and human 14-3-3ε (PDB: 2BR9) as templates, respectively 50. The 3-D coordinates of the TVS167 peptide (phosphorylated and non-phosphorylated) were prepared with the PyMOL Molecular Graphics System V. 1.3 (Schrödinger, Portland, Oreg.). The 3D coordinates of the Ph-TVS167 were extracted from the crystal structure of human 14-3-3ε in complex with phospho-peptide ligand (PDB: 2BR9), and then virtually mutated. Docking of the peptide with the 14-3-3ε protein was performed with AutoDock-vina 51. Protein-protein docking between mouse VDAC1 and 14-3-3ε was performed with HEX V 6.3. All docking results and protein structures are presented either in the PyMOL Molecular Graphics System and/or in Swiss-PDB viewer 4.1.

Statistical analysis. Experimental results were examined for significance by two-tailed t-tests (FIGS. 1b, c, 2f, g, 3b, c, e, g, i, j, 4b, c, f, 5a, b, 7b, c) or one-way ANOVA (FIGS. 1d, 2e, 3a, e, f) with GraphPad Prism 5 software. Cells from three independent passages (n=3) were included for each experiment that involved MA-10 and NCL-H295R cells, and each passage was examined in triplicate in each experiment. In the ex vivo testes cultures, three and four animals were included for the control and TVS167 or TVG167 treatment respectively (n=3 or 4). For bolus dose-response testicular injections, three animals were used for each dose (n=3). Five animals (n=5) were included for each pump installation of different groups involving water, TVS167, or TVS167-releasing pumps. Three animals (n=3) were included per group for i.p. injections of water or Cetrorelix™. Six animals (n=6) were included per group for water or Cetrorelix injections followed by water or TVS167 pump installation.

14-3-3ε negatively regulates steroidogenesis. The hormone-responsive MA-10 mouse Leydig tumor cells were used to study the role of 14-3-3ε in steroidogenesis. Immunocytochemistry (ICC) indicated that 14-3-3ε was present and partially colocalized with mitochondria in MA-10 mouse tumor Leydig cells (FIG. 1a). Immunoblot analysis indicated that the cAMP analog 8-Bromo-cAMP (8-Br-cAMP), which triggers maximal steroidogenesis, did not alter 14-3-3ε levels in MA-10 cells after 120 min of treatment which is a time point at which the increase in the rate of steroidogenesis is highest (FIG. 1b), However, Blue-Native polyacrylamide gel electrophoresis followed by immunoblot of isolated mitochondrial complexes from hormone-treated MA-10 cells showed a 5-fold induction in 14-3-3ε levels compared to control; a finding confirmed by mass spectrometry of the isolated protein complexes (Aghazadeh et al. 2012).

To understand the physiological role of 14-3-3ε in steroidogenesis, 14-3-3ε was knocked down with specific small interfering RNA (siRNA) (Table 1). Scrambled and hypoxanthine-guanine phosphoribosyl transferase siRNAs served as negative and positive controls, respectively. MA-10 cells were transfected with 5, 10, or 20 nM siRNA to optimize knockdown (K/D). Ultimately, 10 nM siRNA achieved 55-75% K/D of 14-3-3ε and was selected for transfection (FIG. 1c). After transfecting 14-3-3ε siRNA, cells were treated with 8-Br-cAMP. Media were collected, and progesterone production was measured by radioimmunoassay (RIA). Treatment with 8-Br-cAMP for 120 min increased progesterone formation by 3-fold in cells with 14-3-3ε K/D compared to controls, suggesting that 14-3-3ε negatively regulated steroidogenesis (FIG. 1d). These results suggest that, unlike 14-3-3γ, 14-3-3ε levels are not induced by hormone treatment and this protein may act as a negative regulator blocking maximal steroid formation.

Figure 2A:
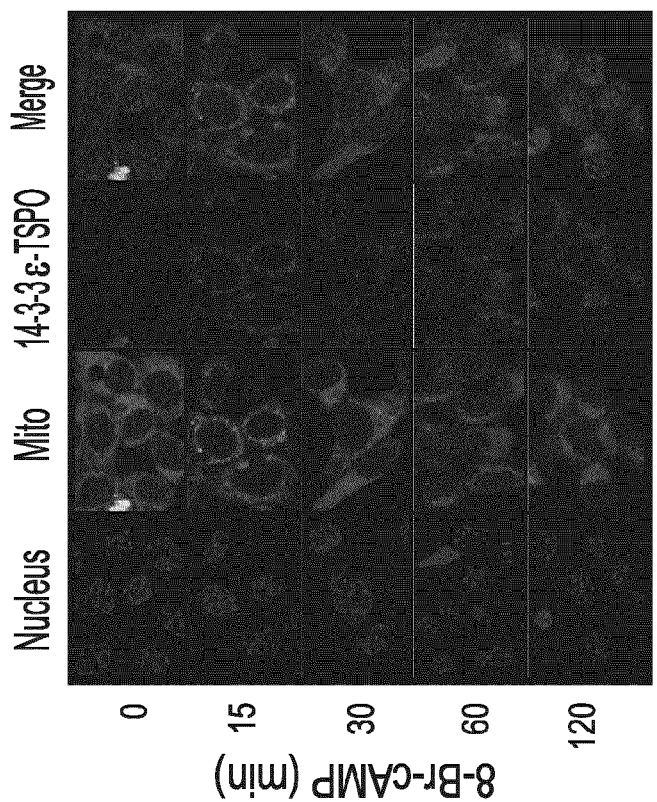

Identification of targets of 14-3-3ε negative regulation. In silico analysis of mouse TSPO, VDAC1, and STAR confirmed 14-3-3 binding motifs (mode I, RSXpSXP (SEQ ID NO: 1); mode II: RXXXpSXP (SEQ ID NO: 2)) on TSPO adjacent to the CRAC domain on VDAC1 at its dimerization and lateral sites and on STAR at its cleavage and activation sites (FIG. 8a). All motifs varied by one to two amino acids from the classic 14-3-3 motif, leading to high affinity but transient binding to 14-3-3 proteins. To identify isoform-specific targets of 14-3-3ε, in vitro co-immunoprecipitation (co-IP) was performed using magnetic beads coupled with 14-3-3ε isoform-specific anti-sera 29 (FIG. 8b). MA-10 cells were treated with 8-Br-cAMP. Transient interactions between 14-3-3ε and target proteins were strengthened by cross-linking with photo-activatable amino acids and ultraviolet (UV) light. Protein lysates precipitated with 14-3-3ε anti-sera were separated by SDS-PAGE, and interactions of 14-3-3ε with TSPO, STAR, and VDAC1 were assessed. Dimerization of 14-3-3ε was reduced by 8-Br-cAMP and reached a minimum after 120 min. Interactions between 14-3-3ε and TSPO were triggered by 8-Br-cAMP but were not time-dependent. In contrast, interactions between 14-3-3ε and STAR or VDAC1 peaked after 15-30 min and 120 min, respectively (FIG. 8b). Co-IP did not appear to be sufficiently sensitive to capture 14-3-3ε targets, therefore, in cell IP (Fredriksson et al. 2002) was performed. Interactions between 14-3-3ε and TSPO were triggered within 15 min of 8-Br-cAMP treatment and were maintained (FIG. 2a, e). Interactions between 14-3-3ε and STAR increased at earlier time points but decreased after 120 min of 8-Br-cAMP treatment (FIG. 2b, f). This pattern was opposite to that observed for 14-3-3ε and VDAC1, as these proteins had reduced interactions at earlier treatment times and significantly increased interactions at 120 min (FIG. 2c, g). Interestingly, the negative regulatory function of 14-3-3ε in steroidogenesis was also observed at 120 min. Thus, VDAC1 appears to be a 14-3-3ε target and mediator of 14-3-3ε effects. The background signal is shown in FIG. 2d.

Figure 9A:
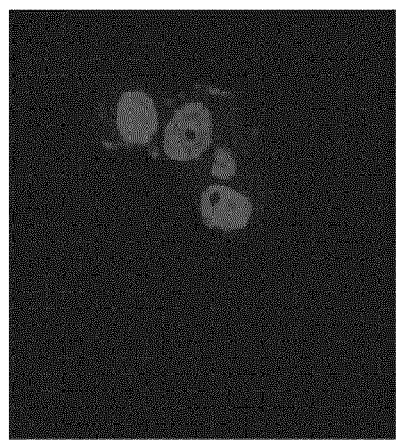
FIG. 9 provides an immunofluorescence image of control MA-10 cells (a) and MA-10 cells treated with the fluorescent FAM-TVS167 chimeric peptide (b), indicating the high efficiency of these peptides to penetrate cell membranes.
Figure 9B:
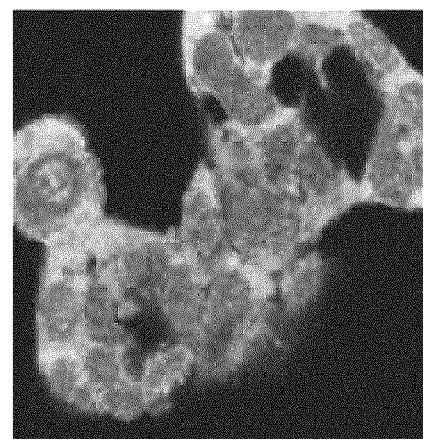

Identification and manipulation of 14-3-3ε-vdac1 interactions. To identify the 14-3-3ε-specific site of interaction with VDAC1, part of HIV transcription factor 1 (TAT) was fused with each of the in silico-predicted 14-3-3-binding motifs on VDAC1 to create TAT-VDAC1 Ser35 (TVS35) and TAT-VDAC1 Ser167 (TVS167) (Table 2). The TAT sequence easily penetrates the cell membrane (Nagahara et al. 1998) and shuttles the conjugated peptide. Serine residues are important for 14-3-3 binding (Aitken 2006) and were mutated to create TAT-VDAC1 Gly35 (TVG35) and TAT-VDAC1 Gly167 (TVG167) control peptides (Table 2). TVS167 was fluorescently labeled. Confocal microscopy indicated that 250 nM TVS167 penetrated into all of the MA-10 cells within 90 min (FIG. 9). MA-10 cells were then incubated in media with TV peptides. Maximal 14-3-3ε-VDAC1 interactions were induced by 120 min of 8-Br-cAMP treatment. Cells were fixed, and in cell IP studies were performed to measure interactions between 14-3-3ε and endogenous VDAC1 in the presence of each peptide. TVS35 and TVS167 competed with VDAC1 for binding 14-3-3ε, resulting in reduced interactions between endogenous 14-3-3ε and VDAC1 (FIG. 3a, b). TVG35 also interacted with 14-3-3ε. However, TVG167-14-3-3ε interactions were much lower, allowing endogenous VDAC1 and 14-3-3ε to interact (FIG. 3a, b).

Figure 10A:
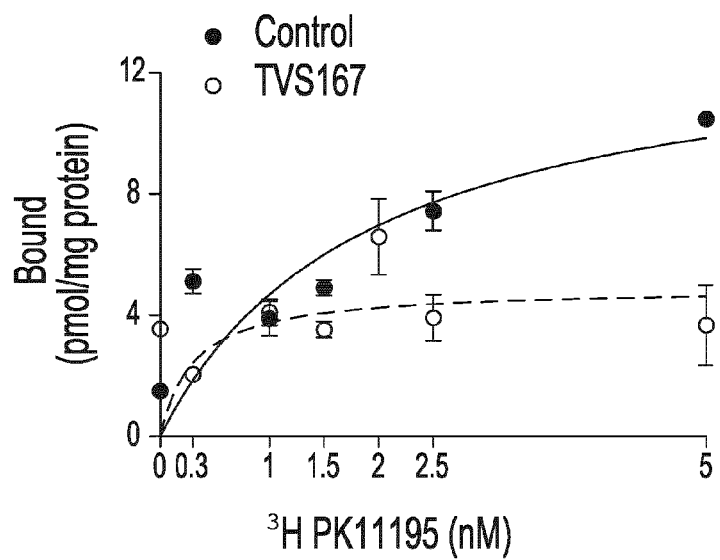
FIG. 10 illustrates that 14-3-3ε regulates the affinity of TSPO for its drug ligand PK11195. (a) Levels (measured as pmol/mg protein) of TSPO bound to PK11195 in the absence (●) or presence (○) of the TVS167 peptide at different doses of $^3$H PK 11195. (b) Kd (measured as nM), affinity$^{-1}$ of TSPO for PK 11195, was measured in the absence (control, white bar) or presence (TVS167, black bar) of TVS167. *** P<0.001 (c) $B_{max}$ (measured as pmol/mg protein), the available binding site of TSPO for PK 11195, was measured in the absence (control, white bar) or presence (TV167, black bar) of TVS167.
Figure 10B:
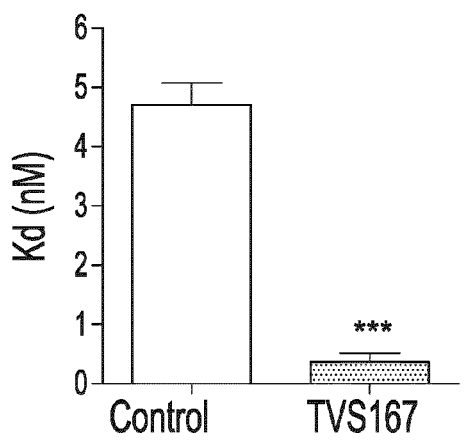
Figure 10C:
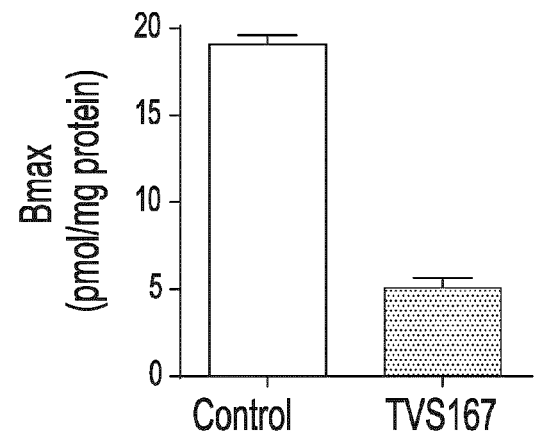

Disruption of 14-3-3ε-VDAC1 interaction at S167, but not S35, induced steroid formation similar to that observed by 14-3-3ε K/D (FIG. 3c). The interactions between 14-3-3ε-STAR and TSPO-VDAC1 were measured in the presence of TVS167 and 8-Br-cAMP. Disruption of VDAC1-14-3-3ε interaction inhibited binding of STAR to 14-3-3ε (FIG. 3d, e), suggesting that VDAC1 and STAR interact with 14-3-3ε at the same site, explaining the opposite patterns of interactions between these proteins and 14-3-3ε (FIG. 2b, c, f, g). Interestingly, TSPO-VDAC1 interactions were increased in the presence of TVS167. These data suggest that the 14-3-3ε scaffold intercalates between TSPO and VDAC1, blocking interactions that mediate cholesterol import across the OMM. Therefore, 14-3-3ε buffers cholesterol import to mitochondria (FIG. 3f, g). TVS167 increased interactions between 14-3-3ε and TSPO by 1.6-fold (FIG. 3h, i). Cholesterol binding to TSPO was blocked with 19-Atriol, a drug that targets the CRAC domain and decreases steroidogenesis. The stimulatory effect of TVS167 was blocked by 19-Atriol, suggesting that interactions between 14-3-3ε and TSPO affected cholesterol binding to TSPO (FIG. 3j). The binding of PK 11195, the most prominent TSPO drug ligand was altered showing increased affinity and reduced binding capacity (FIG. 10). Thus, 14-3-3ε appears to regulate the microenvironment of TSPO. Therefore the interaction between 14-3-3ε and TSPO is critical for steroidogenesis.

Figure 11A:
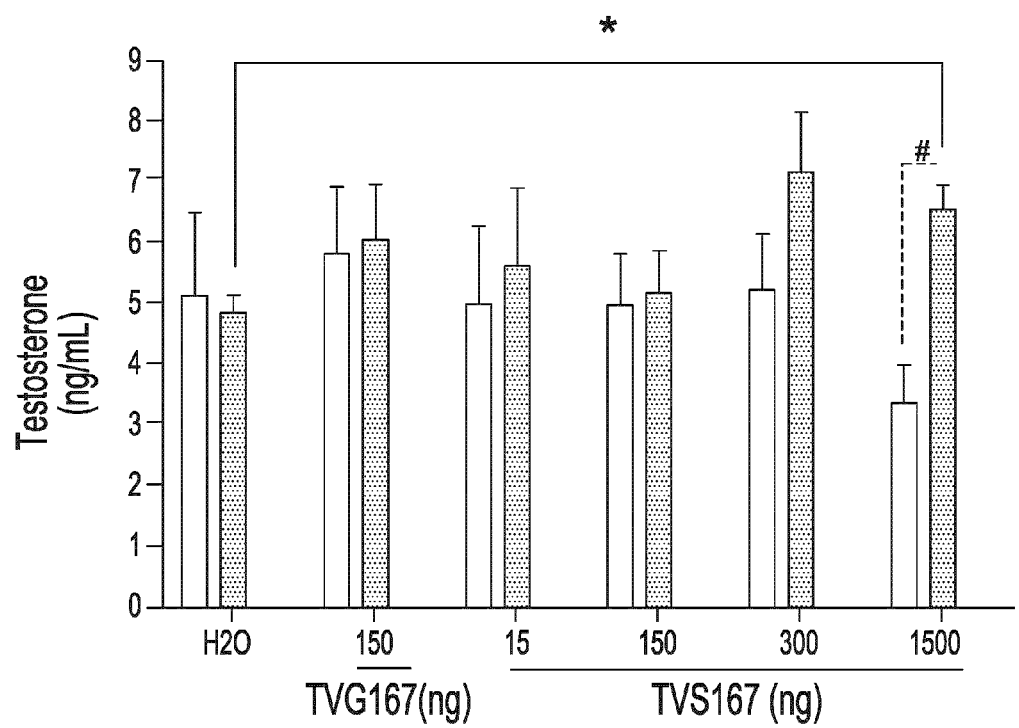
FIG. 11 shows that TVS167 induces T levels in a dose response manner. One testis of each adult Sprague-Dawley rat was injected with a bolus of water, TVG167, or different doses of TVS167. The other testis was used as a control. T levels were measured after 2 hrs in the intratesticular fluid of each treated testis (black bars) and, control testis (white bars) (a). * P<0.05. Serum LH levels (b) were also monitored. * or # P<0.05.
Figure 11B:
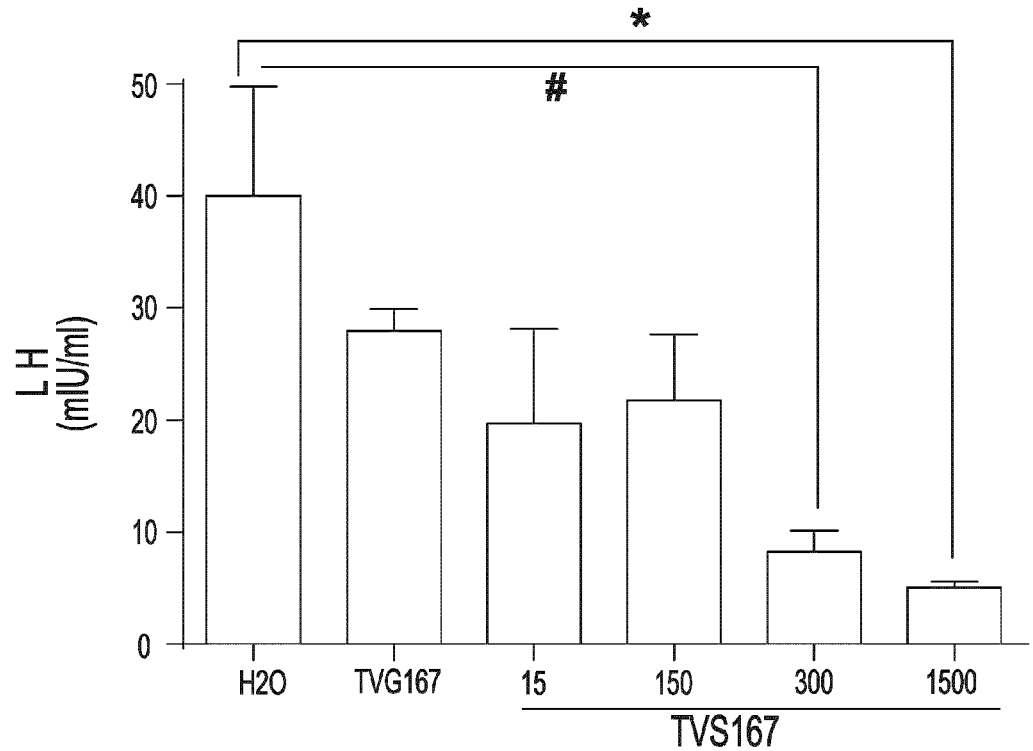
Figure 12A:
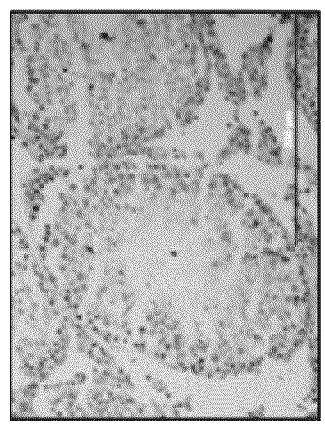
FIG. 12 shows that the administration of the TVS167 peptides does not induce toxic histological modifications to the testis. Rat testes sections were obtained from wild type adult Sprague-Dawley rats and rats injected with a bolus does of $H_2O$ or 150 ng TVS167 following implantation of $H_2O$ or TVS167 (75 ng/24 h) releasing pump. The pumps were directed to one testis. Animals were dissected 24 h post pump implantation and sectioned. Hematoxylin staining of these sections indicates no histological difference between testes of these animals (a, control, b, $H_2O$ pump and c, TVS167 pump).
Figure 12B:
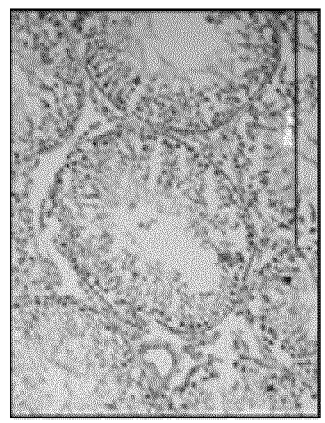
Figure 12C:
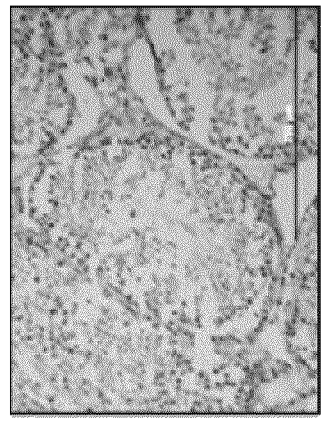

TV peptides penetrate rat testes and induce T production ex vivo and in vivo in an LH-independent manner. Testes from adult Sprague-Dawley rats were collected and cultured ex vivo to assess the potential of the TV peptides to penetrate the testes and induce Leydig cell androgen formation. Testes were maintained in media with 250 nM TV peptides for 90 min followed by treatment with or without hCG for 120 min. TV peptides penetrated the rat testes, and TVS167 treatment induced T production (FIG. 4a). Interestingly, testes treated with TVS167 produced significantly more T than hCG-treated controls. Rats were then injected in one testis with water, 150 ng TVG167, or 15, 150, 300, or 1500 ng TVS167. The contralateral testis was used as a control. Blood and testes were collected 2 hrs after injection, and T levels were measured in the intratesticular fluid and serum by RIA. T levels increased in a dose-dependent manner in testes treated with TV peptides, whereas the contralateral testes of the same animals used as control, had reduced T levels. This trend began at 300 ng dose and reached significance with 1500 ng TVS167, suggesting that LH negative feedback is triggered at these doses (FIG. 11a). Therefore LH levels were measured, showing that in the presence of 300-1500 ng TVS167 increased T production led to the suppression of circulating LH levels (FIG. 11b). Thus, 150 ng TVS167, the highest dose that does not affect LH levels was further used. To induce and maintain T production over longer periods of time, a 150-ng bolus of T was injected into one testis of each rat. Alzet mini-osmotic pumps containing water (TV peptide diluent), TVG167, or TVS167 were surgically implanted in the abdomen and directed to the injected testis with a small catheter. The contralateral testis served as control. Pumps released 75 ng TVS/G167 (250 nM) over 24 hrs. T levels in interstitial fluid and serum and also circulating LH levels were measured. Animals treated with TVS167 had significantly higher levels of T in interstitial fluid and serum, whereas LH levels were significantly reduced compared to controls (FIG. 4b, c, d). In vivo VDAC1-14-3-3ε interactions were studied through in cell IP in the testes of control and rats implanted with water- or TVS167-releasing pumps. TVS167 treatment blocked 14-3-3ε-VDAC1 interactions (FIG. 4e). No morphological differences were seen between rat testis from controls or from animals implanted with water or TVS167-releasing pumps (FIG. 12).

The in vivo induction of T by TVS167 is LH-independent. It was then examined if TVS167 triggers T production in animals with very low LH levels. The gonadotropin-releasing hormone (GnRH) antagonist Cetrorelix™ was intraperitoneally (i.p.) injected into 60-64 day-old rats at 0.4 mg/day for four days as previously described (Horvath et al. 2004). T levels were completely suppressed in the testes and serum four days after injection (FIG. 5a, b; no pump). Next, Cetrorelix™ was injected i.p. for 0-4 days while on day 3 animals were injected in one testis with 150 ng TVS167 and implanted with TVS167-releasing pump. Animals were sacrificed after 24 hrs. T levels increased by 12-, 8-, or 20-fold, respectively, in testes connected to a TVS167 pump, testes not connected to a pump (due to diffusion) and in both testes together (FIG. 5a+, –, Total). TVS167 treatment increased circulating T by 5-fold (FIG. 5b).

To further assess the link between VDAC1 and TSPO function in vivo, the acute effect of TVS167 was compared to that of a well characterized high affinity TSPO drug ligand, N,N-dihexyl-2-(4-fluorophenyl)indole-3-acetamide (FGIN-1-27) (Perheentupa et al. 2009), in the absence of LH signaling. Sprague-Dawley rats of 68-72 days old were given an i.p. injected of either $H_2O$ or 0.4 mg Cetrorelix™ for 0-4 days. On day 4, a bolus intratesticular injection of 8.5 µg FGIN-1-27 or its solvent (control) was given to one testis per animal. To assess the acute effect of this TSPO drug ligand on steroidogenesis intratesticular and circulating T levels were measured after 2 hrs. The results obtained showed a significant increase in intratesticular T levels in both control and Cetrorelix-treated rats (FIG. 5c) whereas plasma T levels were increased only in the Cetrorelix-treated animals (FIG. 5d). It should be noted that a 2 hrs bolus intratesticular injection of TVS167 peptide to control Sprague-Dawley rats also resulted in an increase in circulating T levels (FIG. 11a).

Figure 6A:
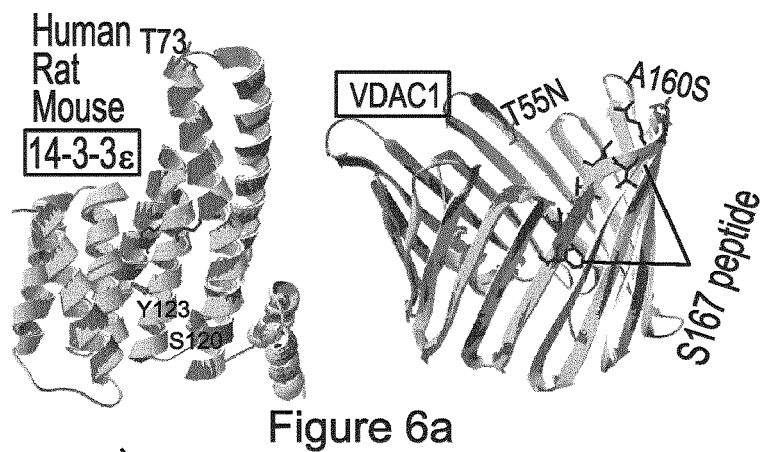
FIG. 6 illustrates a modeling representation of the human VDAC1 14-3-3ε motif containing S167. (a) Putative models 14-3-3ε and VDAC1 were mapped in indicated species showing a high degree of homology. (b) Macromolecular docking among two proteins. The docking site of 14-3-3ε in the VDAC1 structure in *Mus musculus* was predicted. TVS167 was shown to dock onto open and non-ligand-bound 14-3-3ε at the site to which VDAC1 also bound to this protein, suggesting that TV167 can block this interaction. Due to a high percentage of homology between the 3-D structures of human 14-3-3ε and VDAC1, the same docking sites were predicted in these species. The ribbon representative of each protein and surface mapping of electrostatic potential of mouse 14-3-3ε are shown. The molecular surface are corresponding to negative, positive and neutral charged regions, respectively. (c, d) The molecular docking studies show TVS167 targets the 14-3-3ε binding groove as well as the right shoulder that interacts with VDAC1 (6b). (e) Mutation of S167 to G167 removes the ability of the TV peptide to dock outside the binding groove. (f) The phosphorylated TVS167 docked within the binding groove.
Figure 6B:
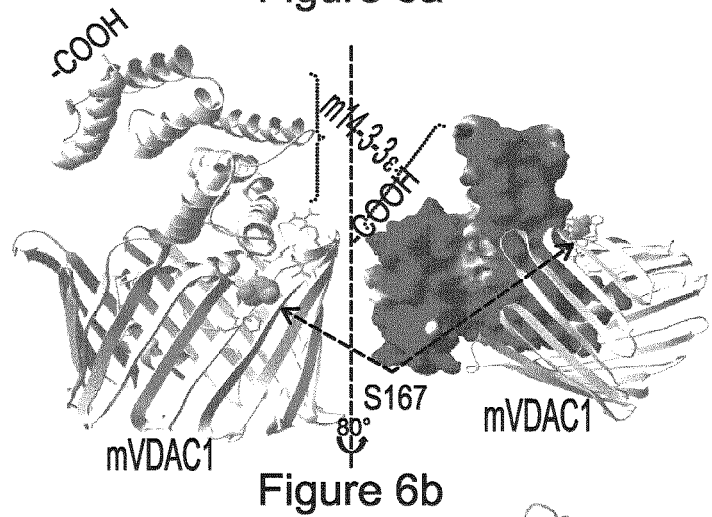
Figure 6C:
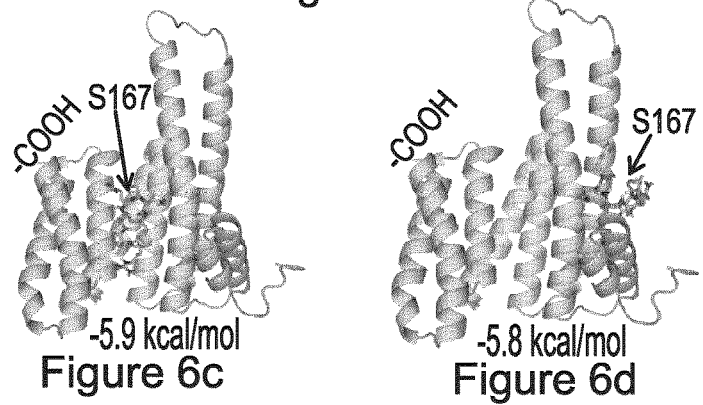
Figure 6D:
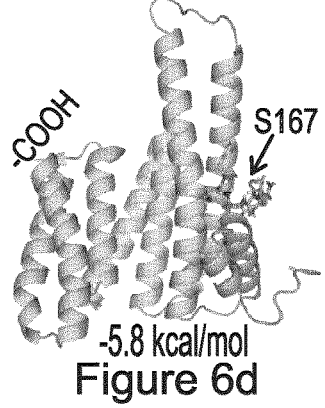
Figure 6E:
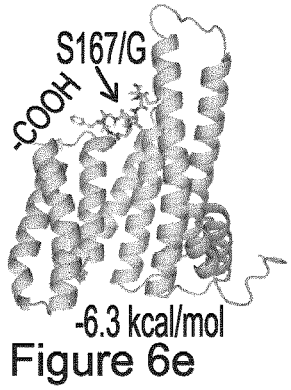
Figure 6F:
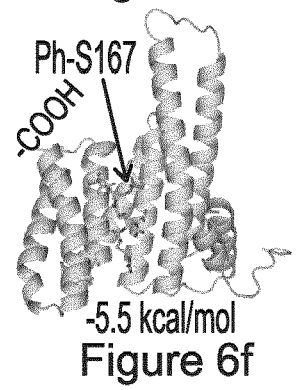

Prediction of TVS167 binding to 14-3-3ε in different species. Sequence alignment showed high (>99%) homology between *Mus musculus, Homo sapiens* and *Rattus norvegicus* 14-3-3ε and VDAC1 proteins. The VDAC1 14-3-3ε binding motif that contains S167 was conserved across species (FIG. 13a, b). The three-dimensional (3-D) structures of human, mouse, and rat VDAC1 and 14-3-3ε were also highly conserved (FIG. 6a). Protein-protein docking predicted the binding site of 14-3-3ε on VDAC1. Surface mapping of electrostatic potential in 14-3-3ε indicates the VDAC1 binding site is involved in protein-protein interaction (FIG. 6b). These data also indicate that S167 is in the mitochondrial membrane suggesting that the interactions of 14-3-3ε with this residue might decrease the conductance of VDAC1 which in turn could affect cholesterol transport. Molecular docking of 14-3-3ε with TVS167 shows the peptide binding within the binding groove with −5.9 kcal/mol affinity (FIG. 6c) and to the right "shoulder" of the 14-3-3ε, the same site as VDAC1 binding site, with −5.8 kcal/mol affinity (FIG. 6d). Similar molecular docking studies indicated that if S167 is mutated to G, the TVG167 peptide falls out of the binding groove, indicating that the mutated peptide is not the favorable ligand of the protein (FIG. 6e). As the most favorable binding site of 14-3-3 proteins to their targets occurs mostly at phosphorylated serine residues, docking studies were performed using the phosphorylated TVS167 peptide (Ph-S167) indicating that the top 9 conformations are all within the binding groove, with 5.5 kcal/mol affinity (FIG. 6θ. Therefore, the most favorable peptide ligand for 14-3-3ε is Ph-TVS167.

Figure 7D:
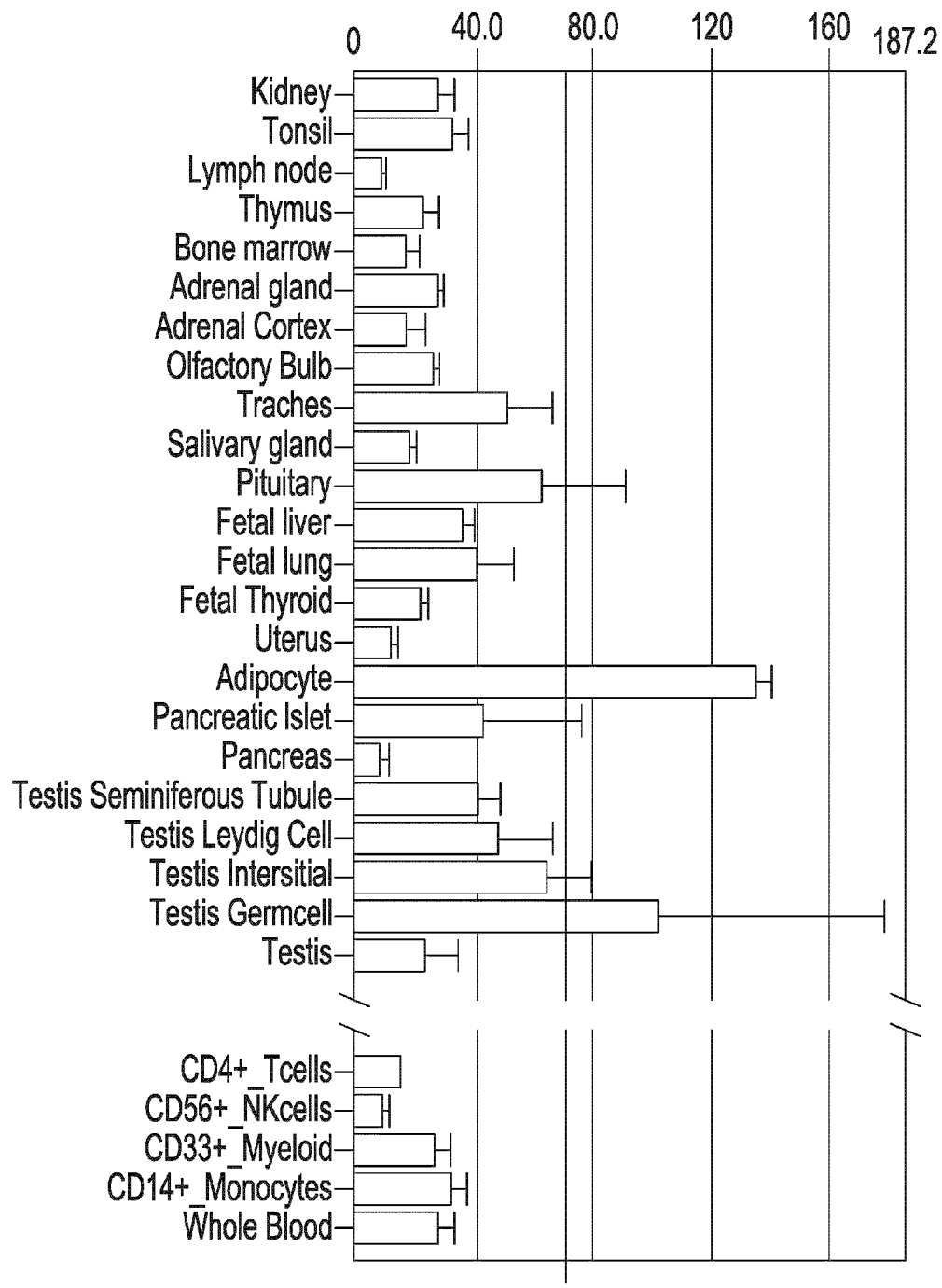
FIG. 7 provides a comparison of 14-3-3ε protein profile in adrenal gland versus testis. (a) Immunofluorescence images illustrates the nucleus and 14-3-3ε expression in sections of adult mice adrenal gland (first row) and testes (second row) indicating higher levels of protein expression in interstitial cells of testes compared to adrenal glands. (b) Immunoblot (b1) and corresponding analysis (b1) show that the expression levels of 14-3-3ε compared to GAPDH are significantly higher in protein lysate extracted from interstitial testes compared of adrenal glands of adult rats. (c) Adult rats were implanted with $H_2O$ (white bar) or TVS167 (black bar) releasing pumps abdominally, this pump was directed to one testis and induces T levels in rat testes and plasma (FIG. 4d, e, f). Corticosterone levels (measured as ng/mL) produced by the adrenal gland cortex were measured in these rats indicating insignificant changes compared to control. (d) Public microarray data comparing mRNA levels of 14-3-3ε in human tissues indicates higher mRNA in human interstitial cells compared to adrenal gland. (e) Duolink assay was performed to study the protein-protein interactions between 14-3-3ε and VDAC1 in NCL-H296R human adrenocortical cell line. Immunofluorescence images illustrate the nucleus (first column), mitochondria (second column) and protein-protein interactions (third column) indicating that the protein-protein interaction signal is not as high as in MA-10 cells and rat testes sections and that despite a decrease in the interactions of 14-3-3ε and VDAC1 in these cells in the presence of TVS167 (second row), this effect is not significant (e1). A corresponding analysis is also presented (e2).

Specificity of TVS167 effects on testicular steroidogenesis. TAT peptides pass through all cell types (Nagahara et al. 1998), and 14-3-3ε is ubiquitously expressed in mammalian tissues. However, expression levels and function of 14-3-3ε are tissue-specific. To gain insights into the effects of TVS167 in other steroid-synthesizing tissues, such as the adrenal gland, 14-3-3ε expression was studied in three mammalian species. Immunohistochemistry was performed on adult mouse testes and adrenals. Testicular interstitial cells were enriched with 14-3-3ε, whereas the levels and concentrations of 14-3-3ε were lower in the steroidogenic adrenal cortex (FIG. 7a). In adult rats, levels of 14-3-3ε were significantly higher in testes than adrenals (FIG. 7b). The effect of TVS167 on corticosterone production was examined in sera from rats implanted with TVS167-releasing pumps for 24 hrs. Significantly higher intratesticular and circulating T levels were found compared to control rats implanted with water-releasing pumps (FIG. 4d, e). Circulating corticosterone levels were not significantly changed by TVS167 (FIG. 7c). Published microarray data indicated that 14-3-3ε mRNA levels were higher in human testes than human adrenals (FIG. 7d). Similar to MA-10 cells, human adrenocortical NCL-H295R cells were treated with or without TVS167 followed by in cell IP to examine 14-3-3ε-VDAC1 interactions. Interactions between 14-3-3ε and VDAC1 were decreased by TVS167. However, this decrease was not significant, possibly because 14-3-3ε levels are lower in NCL-H295R cells (FIG. 7e).

T contributes to quality-of-life and well-being. Male development, virilisation, sexual differentiation, and fertility rely on T production throughout life. A progressive decline in T begins at age 40 (andropause) and continues in aging males. This decline is due in part to an age-related reduction in steroidogenesis by testicular Leydig cells, i.e., primary hypogonadism. A low level of T has been linked with several chronic and life-threatening diseases and is also a major cause of male infertility. TRT shows clinical benefit in patients with andropause in order to ameliorate muscle mass and strength, bone density, libido and quality of erection. However, TRT is not recommended for patients with non-treated or at high risk of prostate cancer, breast cancer, sleep apnea, infertility, cardiovascular problems and hematocrit over 50%. Therefore alternative therapies with fewer side effects are needed.

The transduceosome mediates the rate-limiting step of steroidogenesis, which is cholesterol import from the cytosol to the mitochondria. Defects in aging Leydig cells involve this rate-limiting step. It was speculated that a scaffold protein at the OMM allows spatial and temporal regulation of protein-protein interactions, leading to cholesterol import and steroid formation. It was previously reported that 14-3-3ε is present in the mitochondria of steroidogenic cells. Induction of steroidogenesis triggered movement of 14-3-3ε from the cytosol to the OMM. K/D studies indicated that 14-3-3ε is a negative regulator of steroidogenesis and a potential target for inducing T biosynthesis. 14-3-3ε is primarily in the cytosol associated with STAR at the beginning of steroidogenesis. VDAC1 then competes with STAR to bind to 14-3-3ε. This promotes relocalization of 14-3-3ε to mitochondria and intercalation between TSPO and VDAC1, resulting in reduced cholesterol import into mitochondria. We believe that competition between STAR and VDAC1 for 14-3-3ε binding balances the interactions between TSPO and 14-3-3ε. Disruption of this balance affects the TSPO microenvironment, which disrupts the binding of cholesterol to this protein. Negative regulation by 14-3-3ε occurs in response to interactions with VDAC1. S167 on VDAC1 was the critical amino acid for these interactions. Analyses of in cell protein-protein interactions indicated that TVS167 competed with endogenous VDAC1 to reduce interactions with 14-3-3ε, leading to increased steroidogenesis. Consequently, serum levels of T were elevated. However, this increase was not as pronounced as that observed in testes. Thus, this approach did not jeopardize the ability of testes to retain T and allowed a controlled amount of T to be released into circulation.

GnRH antagonists induce chemical castration by removing LH signaling and blocking T production. Cetrorelix™ blocked LH release and T production in adult rats. Testicular infusion of TVS167 to the testes of Cetrorelix™-treated rats increased T by 20-fold despite a lack of LH. Thus, protein-protein interactions are critical for the production of T by Leydig cells in the absence of LH. These results suggest that TVS167 is a potential therapy for treating primary hypogonadism and for maintaining physiological T levels during situations, such as aging, without requiring exogenous administration of T.

The data presented point to TSPO as the downstream target of the 14-3-3ε-VDAC interactions mediating cholesterol delivery into mitochondria for steroidogenesis. Indeed, TVS167 affected the 14-3-3ε-TSPO interactions, increased the TSPO drug ligand affinity while reducing its binding capacity, and the stimulatory effect of TVS167 on steroid formation was blocked by 19-Atriol, a drug blocking cholesterol binding to TSPO. Moreover, FGIN-1-27, a high affinity TSPO drug ligand induced acute T formation in vivo both in control and Cetrorelix™-treated rats, although to a lesser extent that TVS167, in agreement with recent findings in aged Brown-Norway rat Leydig cells, a model of male hypogonadism.

Although the signal transduction mechanisms mediating the effect of LH on Leydig cell steroidogenesis are well known, the results of this example suggests that alternative mechanisms via intracellular peptide mediators may be involved in the production of T. The presence of such natural intracellular peptides able to regulate protein-protein interactions and cell signal transduction was recently demonstrated.

Homo sapiens, Mus musculus and Rattus norvegicus 14-3-3ε and VDAC1 proteins showed high degrees of homology. In addition, the VDAC1 14-3-3ε binding motif that contains S167 had a 100% across-species homology. Thus, it is highly probable that the bioactive TV presented herein will also induce T formation in humans. In fact, surface mapping of 14-3-3ε indicated that TVS167 binds to the open structure of 14-3-3ε and blocks docking of 14-3-3ε to VDAC1 in all species.

The adrenal is second only to the gonads as a major site of steroid synthesis. Although these tissues share common signaling mechanisms for regulating steroid formation, there are some differences. For example, different lipoproteins supply cholesterol for steroidogenesis, and the adrenal has a rapid stress response to hormones. Tissue-specific roles of 14-3-3ε are well-established 14-3-3ε levels were much lower in the adrenals than in the testes. In addition, interactions between 14-3-3ε and VDAC1 were lower in human adrenocortical cells compared to testes. Moreover, TVS167 significantly increased circulating T levels in rats but failed to induce corticosteroid levels. These results demonstrate the specificity of TVS167 for maintaining testicular function and T formation without affecting the adrenal steroidogenesis.

Taken together the results presented herein not only unveiled a novel mechanism regulating androgen biosynthesis but also identified a novel therapeutic target which upon activation allows for the recovery of the ability of the testis to form androgens. Thus, the identified lead peptide TVS167 offers a new potential means for treating primary hypogonadism and for maintaining physiological T levels when needed, without requiring exogenous administration of T. Considering that in addition to androgens the testis makes a number of other physiologically important steroids, it is obvious that activating the endogenous mechanism of steroid production in testis may offer additional benefits to the administration of a testosterone analog.

While the invention has been described in connection with specific embodiments thereof, it will be understood that the scope of the claims should not be limited by the preferred embodiments set forth in the examples, but should be given the broadest interpretation consistent with the description as a whole.

REFERENCES

U.S. Pat. No. 7,803,351

Aghazadeh, Y. et al. Hormone-induced 14-3-3gamma adaptor protein regulates steroidogenic acute regulatory protein activity and steroid biosynthesis in MA-10 Leydig cells. J. Biol. Chem. (2012).

Aitken, A. 14-3-3 proteins: a historic overview. Semin. Cancer Biol. 16, 162-172 (2006).

Fredriksson, S. et al. Protein detection using proximity-dependent DNA ligation assays. Nat. Biotechnol. 20, 473-477 (2002).

Gegenbauer, K., Elia, G., Blanco-Fernandez, A., & Smolenski, A. Regulator of G-protein signaling 18 integrates activating and inhibitory signaling in platelets. Blood 119, 3799-3807 (2012).

Gwynne, J. T. & Strauss, J. F., III The role of lipoproteins in steroidogenesis and cholesterol metabolism in steroidogenic glands. Endocr. Rev. 3, 299-329 (1982).

Horvath, J. E., Toiler, G. L., Schally, A. V., Bajo, A. M., & Groot, K. Effect of long-term treatment with low doses of the LHRH antagonist Cetrorelix on pituitary receptors for LHRH and gonadal axis in male and female rats. Proc. Natl. Acad. Sci. U. S. A 101, 4996-5001 (2004).

Kramer, B., Rarey, M., & Lengauer, T. CASP2 experiences with docking flexible ligands using FlexX. Proteins Suppl 1, 221-225 (1997).

Nagahara, H. et al. Transduction of full-length TAT fusion proteins into mammalian cells: TAT-p27Kip1 induces cell migration. Nat. Med. 4, 1449-1452 (1998).

Perheentupa, A. & Huhtaniemi, I. Aging of the human ovary and testis. Mol. Cell Endocrinol. 299, 2-13 (2009).

Ritchie, D. W. & Venkatraman, V. Ultra-fast FFT protein docking on graphics processors. Bioinformatics. 26, 2398-2405 (2010).

Trott, O. & Olson, A. J. AutoDock Vina: improving the speed and accuracy of docking with a new scoring function, efficient optimization, and multithreading. J. Comput. Chem. 31, 455-461 (2010).

Yaffe, M. B. et al. The structural basis for 14-3-3:phosphopeptide binding specificity. Cell 91, 961-971 (1997).

What is claimed is:

1. An isolated peptide consisting of a maximum of 13 consecutive amino acid residues and having the amino acid sequence RVTQSNF (SEQ ID NO: 5).

2. The isolated peptide of claim 1, consisting of the amino acid sequence SKSRVTQSNFAVG (SEQ ID NO: 30).

3. The isolated peptide of claim 1, consisting of the amino acid sequence AKSRVTQSNFAVG (SEQ ID NO: 31).

4. The isolated peptide of claim 1, wherein the serine residue at position 5 of SEQ ID NO: 5 is phosphorylated.

5. A chimeric peptide having the isolated peptide of claim 1 fused to a cell penetrating peptide.

6. The chimeric peptide of claim 5, wherein the cell penetrating peptide is from a TAT protein.

7. The chimeric peptide of claim 6, wherein the cell penetrating peptide has the amino acid sequence YGRK-KRRQRRR (SEQ ID NO: 29).

8. The chimeric peptide of claim 5, wherein the carboxy terminus of the cell penetrating peptide is fused to the amino terminus of the isolated peptide.

9. The chimeric peptide of claim 5, wherein the isolated peptide is fused to the cell penetrating peptide by a linker.

10. The chimeric peptide of claim 9, wherein the linker comprises at least one amino acid.

11. The chimeric peptide of claim 10, wherein the linker is a glycine residue.

12. A method for promoting the endogenous production of a steroid in a cell, said method comprising contacting the cell with the isolated peptide of claim 1 so as to promote the endogenous production of the steroid in the cell.

13. The method of claim 12, wherein the steroid is testosterone.

14. The method of claim 12, wherein the cell is in vivo and the method further comprises administering the isolated peptide, to a subject in need thereof comprising the cell.

15. The method of claim 14, wherein the subject is a mammal.

16. The method of claim 15, wherein the subject is a male.

17. The method of claim 12, wherein the cell is from a testis.

18. The method of claim 17, wherein the cell is a Leydig cell.

19. The method of claim 12 for the treatment and/or alleviation of symptoms of a condition associated with hypogonadism.

20. The method of claim 19, wherein the condition associated with hypogonadism is at least one of infertility, aging, decreased libido, sexual dysfunction, altered mood, fatigue, decreased lean body mass, decreased bone mineral density, increased visceral fat or metabolic syndrome.

* * * * *

```
SEQUENCE LISTING

<160> NUMBER OF SEQ ID NOS: 31

<210> SEQ ID NO 1
<211> LENGTH: 7
<212> TYPE: PRT
<213> ORGANISM: Artificial Sequence
<220> FEATURE:
<223> OTHER INFORMATION: 14-3-3 binding motif mode I
<220> FEATURE:
<221> NAME/KEY: VARIANT
<222> LOCATION: (3)..(3)
<223> OTHER INFORMATION: Xaa can be any amino acid
<220> FEATURE:
<221> NAME/KEY: VARIANT
<222> LOCATION: (6)..(6)
<223> OTHER INFORMATION: Xaa can be any amino acid

<400> SEQUENCE: 1

Arg Ser Xaa Pro Ser Xaa Pro
1               5

<210> SEQ ID NO 2
<211> LENGTH: 8
<212> TYPE: PRT
<213> ORGANISM: Artificial Sequence
<220> FEATURE:
<223> OTHER INFORMATION: 14-3-3 binding motif mode II
<220> FEATURE:
<221> NAME/KEY: VARIANT
<222> LOCATION: (2)..(2)
<223> OTHER INFORMATION: Xaa can be any amino acid
<220> FEATURE:
<221> NAME/KEY: VARIANT
<222> LOCATION: (3)..(3)
<223> OTHER INFORMATION: Xaa can be any amino acid
<220> FEATURE:
<221> NAME/KEY: VARIANT
<222> LOCATION: (4)..(4)
<223> OTHER INFORMATION: Xaa can be any amino acid
```

```
<220> FEATURE:
<221> NAME/KEY: VARIANT
<222> LOCATION: (7)..(7)
<223> OTHER INFORMATION: Xaa can be any amino acid

<400> SEQUENCE: 2

Arg Xaa Xaa Xaa Pro Ser Xaa Pro
1               5

<210> SEQ ID NO 3
<211> LENGTH: 5
<212> TYPE: PRT
<213> ORGANISM: Artificial Sequence
<220> FEATURE:
<223> OTHER INFORMATION: 14-3-3 binding motif mode III
<220> FEATURE:
<221> NAME/KEY: VARIANT
<222> LOCATION: (2)..(2)
<223> OTHER INFORMATION: Xaa can be Ser or Pro
<220> FEATURE:
<221> NAME/KEY: VARIANT
<222> LOCATION: (4)..(4)
<223> OTHER INFORMATION: Xaa can be any amino acid except Pro
<220> FEATURE:
<221> NAME/KEY: VARIANT
<222> LOCATION: (5)..(5)
<223> OTHER INFORMATION: Xaa can be any amino acid except Pro

<400> SEQUENCE: 3

Pro Xaa Thr Xaa Xaa
1               5

<210> SEQ ID NO 4
<211> LENGTH: 6
<212> TYPE: PRT
<213> ORGANISM: Artificial Sequence
<220> FEATURE:
<223> OTHER INFORMATION: 14-3-3 motif of mVDAC1

<400> SEQUENCE: 4

Lys Thr Lys Ser Glu Asn
1               5

<210> SEQ ID NO 5
<211> LENGTH: 7
<212> TYPE: PRT
<213> ORGANISM: Artificial Sequence
<220> FEATURE:
<223> OTHER INFORMATION: 14-3-3 motif of mVDAC1

<400> SEQUENCE: 5

Arg Val Thr Gln Ser Asn Phe
1               5

<210> SEQ ID NO 6
<211> LENGTH: 25
<212> TYPE: PRT
<213> ORGANISM: Artificial Sequence
<220> FEATURE:
<223> OTHER INFORMATION: TVS35 peptide

<400> SEQUENCE: 6

Tyr Gly Arg Lys Lys Arg Arg Gln Arg Arg Gly Lys Leu Asp Leu
1               5                   10                  15

Lys Thr Lys Ser Glu Asn Gly Leu Glu
            20                  25

<210> SEQ ID NO 7
```

```
<211> LENGTH: 26
<212> TYPE: PRT
<213> ORGANISM: Artificial Sequence
<220> FEATURE:
<223> OTHER INFORMATION: TVS167 peptide

<400> SEQUENCE: 7

Tyr Gly Arg Lys Lys Arg Arg Gln Arg Arg Gly Thr Ser Lys Ser
1               5                   10                  15

Arg Val Thr Gln Ser Asn Phe Ala Val Gly
            20                  25

<210> SEQ ID NO 8
<211> LENGTH: 25
<212> TYPE: PRT
<213> ORGANISM: Artificial Sequence
<220> FEATURE:
<223> OTHER INFORMATION: TVG35 peptide

<400> SEQUENCE: 8

Tyr Gly Arg Lys Lys Arg Arg Gln Arg Arg Gly Lys Leu Asp Leu
1               5                   10                  15

Lys Thr Lys Gly Glu Asn Gly Leu Glu
            20                  25

<210> SEQ ID NO 9
<211> LENGTH: 26
<212> TYPE: PRT
<213> ORGANISM: Artificial Sequence
<220> FEATURE:
<223> OTHER INFORMATION: TVG167 peptide

<400> SEQUENCE: 9

Tyr Gly Arg Lys Lys Arg Arg Gln Arg Arg Gly Thr Ser Lys Ser
1               5                   10                  15

Arg Val Thr Gln Gly Asn Phe Ala Val Gly
            20                  25

<210> SEQ ID NO 10
<211> LENGTH: 7
<212> TYPE: PRT
<213> ORGANISM: Artificial Sequence
<220> FEATURE:
<223> OTHER INFORMATION: 14-3-3 motif

<400> SEQUENCE: 10

Arg Arg Arg Ser Ser Leu Leu
1               5

<210> SEQ ID NO 11
<211> LENGTH: 7
<212> TYPE: PRT
<213> ORGANISM: Artificial Sequence
<220> FEATURE:
<223> OTHER INFORMATION: 14-3-3 motif

<400> SEQUENCE: 11

Arg Asp Phe Val Ser Val Arg
1               5

<210> SEQ ID NO 12
<211> LENGTH: 6
<212> TYPE: PRT
<213> ORGANISM: Artificial Sequence
<220> FEATURE:
<223> OTHER INFORMATION: 14-3-3 motif
```

```
<400> SEQUENCE: 12

Arg Arg Gly Ser Thr Cys
1               5

<210> SEQ ID NO 13
<211> LENGTH: 6
<212> TYPE: PRT
<213> ORGANISM: Artificial Sequence
<220> FEATURE:
<223> OTHER INFORMATION: 14-3-3 motif

<400> SEQUENCE: 13

Lys Thr Lys Ser Glu Asn
1               5

<210> SEQ ID NO 14
<211> LENGTH: 7
<212> TYPE: PRT
<213> ORGANISM: Artificial Sequence
<220> FEATURE:
<223> OTHER INFORMATION: 14-3-3 motif

<400> SEQUENCE: 14

Arg Val Thr Gln Ser Asn Phe
1               5

<210> SEQ ID NO 15
<211> LENGTH: 7
<212> TYPE: PRT
<213> ORGANISM: Artificial Sequence
<220> FEATURE:
<223> OTHER INFORMATION: 14-3-3 motif

<400> SEQUENCE: 15

Arg Trp Tyr Ala Ser Leu Gln
1               5

<210> SEQ ID NO 16
<211> LENGTH: 7
<212> TYPE: PRT
<213> ORGANISM: Artificial Sequence
<220> FEATURE:
<223> OTHER INFORMATION: 14-3-3 motif

<400> SEQUENCE: 16

Arg Gly Gly Ser Arg Leu Pro
1               5

<210> SEQ ID NO 17
<211> LENGTH: 255
<212> TYPE: PRT
<213> ORGANISM: Mus musculus

<400> SEQUENCE: 17

Met Asp Asp Arg Glu Asp Leu Val Tyr Gln Ala Lys Leu Ala Glu Gln
1               5                   10                  15

Ala Glu Arg Tyr Asp Glu Met Val Ser Met Lys Lys Val Ala Gly
                20                  25                  30

Met Asp Val Glu Leu Thr Val Glu Arg Asn Leu Leu Ser Val Ala
            35                  40                  45

Tyr Lys Asn Val Ile Gly Ala Arg Arg Ala Ser Trp Arg Ile Ile Ser
        50                  55                  60

Ser Ile Glu Gln Lys Glu Glu Asn Lys Gly Gly Glu Asp Lys Leu Lys
```

```
                65                  70                  75                  80
            Met Ile Arg Glu Tyr Arg Gln Met Val Glu Thr Glu Leu Lys Leu Ile
                                85                  90                  95

Cys Cys Asp Ile Leu Asp Val Leu Asp Lys His Leu Ile Pro Ala Ala
                            100                 105                 110

Asn Thr Gly Glu Ser Lys Val Phe Tyr Lys Met Lys Gly Asp Tyr
                        115                 120                 125

His Arg Tyr Leu Ala Glu Phe Ala Thr Gly Asn Asp Arg Lys Glu Ala
                        130                 135                 140

Ala Glu Asn Ser Leu Val Ala Tyr Lys Ala Ala Ser Asp Ile Ala Met
            145                 150                 155                 160

Thr Glu Leu Pro Pro Thr His Pro Ile Arg Leu Gly Leu Ala Leu Asn
                            165                 170                 175

Phe Ser Val Phe Tyr Tyr Glu Ile Leu Asn Ser Pro Asp Arg Ala Cys
                        180                 185                 190

Arg Leu Ala Lys Ala Ala Phe Asp Asp Ala Ile Ala Glu Leu Asp Thr
                        195                 200                 205

Leu Ser Glu Glu Ser Tyr Lys Asp Ser Thr Leu Ile Met Gln Leu Leu
                        210                 215                 220

Arg Asp Asn Leu Thr Leu Trp Thr Ser Asp Met Gln Gly Asp Gly Glu
            225                 230                 235                 240

Glu Gln Asn Lys Glu Ala Leu Gln Asp Val Glu Asp Glu Asn Gln
                            245                 250                 255

<210> SEQ ID NO 18
<211> LENGTH: 255
<212> TYPE: PRT
<213> ORGANISM: Homo sapiens

<400> SEQUENCE: 18

Met Asp Asp Arg Glu Asp Leu Val Tyr Gln Ala Lys Leu Ala Glu Gln
1               5                   10                  15

Ala Glu Arg Tyr Asp Glu Met Val Glu Ser Met Lys Lys Val Ala Gly
                20                  25                  30

Met Asp Val Glu Leu Thr Val Glu Glu Arg Asn Leu Leu Ser Val Ala
            35                  40                  45

Tyr Lys Asn Val Ile Gly Ala Arg Arg Ala Ser Trp Arg Ile Ile Ser
        50                  55                  60

Ser Ile Glu Gln Lys Glu Glu Asn Lys Gly Gly Glu Asp Lys Leu Lys
65                  70                  75                  80

Met Ile Arg Glu Tyr Arg Gln Met Val Glu Thr Glu Leu Lys Leu Ile
                85                  90                  95

Cys Cys Asp Ile Leu Asp Val Leu Asp Lys His Leu Ile Pro Ala Ala
            100                 105                 110

Asn Thr Gly Glu Ser Lys Val Phe Tyr Tyr Lys Met Lys Gly Asp Tyr
        115                 120                 125

His Arg Tyr Leu Ala Glu Phe Ala Thr Gly Asn Asp Arg Lys Glu Ala
        130                 135                 140

Ala Glu Asn Ser Leu Val Ala Tyr Lys Ala Ala Ser Asp Ile Ala Met
145                 150                 155                 160

Thr Glu Leu Pro Pro Thr His Pro Ile Arg Leu Gly Leu Ala Leu Asn
                165                 170                 175

Phe Ser Val Phe Tyr Tyr Glu Ile Leu Asn Ser Pro Asp Arg Ala Cys
            180                 185                 190
```

Arg Leu Ala Lys Ala Ala Phe Asp Asp Ala Ile Ala Glu Leu Asp Thr
            195                 200                 205

Leu Ser Glu Glu Ser Tyr Lys Asp Ser Thr Leu Ile Met Gln Leu Leu
        210                 215                 220

Arg Asp Asn Leu Thr Leu Trp Thr Ser Asp Met Gln Gly Asp Gly Glu
225                 230                 235                 240

Glu Gln Asn Lys Glu Ala Leu Gln Asp Val Glu Asp Glu Asn Gln
            245                 250                 255

<210> SEQ ID NO 19
<211> LENGTH: 255
<212> TYPE: PRT
<213> ORGANISM: Rattus norvegicus

<400> SEQUENCE: 19

Met Asp Asp Arg Glu Asp Leu Val Tyr Gln Ala Lys Leu Ala Glu Gln
1               5                   10                  15

Ala Glu Arg Tyr Asp Glu Met Val Glu Ser Met Lys Lys Val Ala Gly
            20                  25                  30

Met Asp Val Glu Leu Thr Val Glu Glu Arg Asn Leu Leu Ser Val Ala
        35                  40                  45

Tyr Lys Asn Val Ile Gly Ala Arg Arg Ala Ser Trp Arg Ile Ile Ser
    50                  55                  60

Ser Ile Glu Gln Lys Glu Asn Lys Gly Gly Glu Asp Lys Leu Lys
65                  70                  75                  80

Met Ile Arg Glu Tyr Arg Gln Met Val Glu Thr Glu Leu Lys Leu Ile
                85                  90                  95

Cys Cys Asp Ile Leu Asp Val Leu Asp Lys His Leu Ile Pro Ala Ala
            100                 105                 110

Asn Thr Gly Glu Ser Lys Val Phe Tyr Tyr Lys Met Lys Gly Asp Tyr
        115                 120                 125

His Arg Tyr Leu Ala Glu Phe Ala Thr Gly Asn Asp Arg Lys Glu Ala
    130                 135                 140

Ala Glu Asn Ser Leu Val Ala Tyr Lys Ala Ala Ser Asp Ile Ala Met
145                 150                 155                 160

Thr Glu Leu Pro Pro Thr His Pro Ile Arg Leu Gly Leu Ala Leu Asn
                165                 170                 175

Phe Ser Val Phe Tyr Tyr Glu Ile Leu Asn Ser Pro Ser Arg Ala Cys
            180                 185                 190

Arg Leu Ala Lys Ala Ala Phe Asp Asp Ala Ile Ala Glu Leu Asp Thr
        195                 200                 205

Leu Ser Glu Glu Ser Tyr Lys Asp Ser Thr Leu Ile Met Gln Leu Leu
    210                 215                 220

Arg Asp Asn Leu Thr Leu Trp Thr Ser Asp Met Gln Gly Asp Gly Glu
225                 230                 235                 240

Glu Gln Asn Lys Glu Ala Leu Gln Asp Val Glu Asp Glu Asn Gln
                245                 250                 255

<210> SEQ ID NO 20
<211> LENGTH: 283
<212> TYPE: PRT
<213> ORGANISM: Mus musculus

<400> SEQUENCE: 20

Met Ala Val Pro Pro Thr Tyr Ala Asp Leu Gly Lys Ser Ala Arg Asp
1               5                   10                  15

Val Phe Thr Lys Gly Tyr Gly Phe Gly Leu Ile Lys Leu Asp Leu Lys
            20                  25                  30

Thr Lys Ser Glu Asn Gly Leu Glu Phe Thr Ser Ser Gly Ser Ala Asn
        35                  40                  45

Thr Glu Thr Thr Lys Val Asn Gly Ser Leu Glu Thr Lys Tyr Arg Trp
    50                  55                  60

Thr Glu Tyr Gly Leu Thr Phe Thr Glu Lys Trp Asn Thr Asp Asn Thr
65                  70                  75                  80

Leu Gly Thr Glu Ile Thr Val Glu Asp Gln Leu Ala Arg Gly Leu Lys
                85                  90                  95

Leu Thr Phe Asp Ser Ser Phe Ser Pro Asn Thr Gly Lys Lys Asn Ala
            100                 105                 110

Lys Ile Lys Thr Gly Tyr Lys Arg Glu His Ile Asn Leu Gly Cys Asp
        115                 120                 125

Val Asp Phe Asp Ile Ala Gly Pro Ser Ile Arg Gly Ala Leu Val Leu
    130                 135                 140

Gly Tyr Glu Gly Trp Leu Ala Gly Tyr Gln Met Asn Phe Glu Thr Ser
145                 150                 155                 160

Lys Ser Arg Val Thr Gln Ser Asn Phe Ala Val Gly Tyr Lys Thr Asp
                165                 170                 175

Glu Phe Gln Leu His Thr Asn Val Asn Asp Gly Thr Glu Phe Gly Gly
            180                 185                 190

Ser Ile Tyr Gln Lys Val Asn Lys Leu Glu Thr Ala Val Asn Leu
        195                 200                 205

Ala Trp Thr Ala Gly Asn Ser Asn Thr Arg Phe Gly Ile Ala Ala Lys
210                 215                 220

Tyr Gln Val Asp Pro Asp Ala Cys Phe Ser Ala Lys Val Asn Asn Ser
225                 230                 235                 240

Ser Leu Ile Gly Leu Gly Tyr Thr Gln Thr Leu Lys Pro Gly Ile Lys
                245                 250                 255

Leu Thr Leu Ser Ala Leu Leu Asp Gly Lys Asn Val Asn Ala Gly Gly
            260                 265                 270

His Lys Leu Gly Leu Gly Leu Glu Phe Gln Ala
        275                 280

<210> SEQ ID NO 21
<211> LENGTH: 283
<212> TYPE: PRT
<213> ORGANISM: Homo sapiens

<400> SEQUENCE: 21

Met Ala Val Pro Pro Thr Tyr Ala Asp Leu Gly Lys Ser Ala Arg Asp
1               5                   10                  15

Val Phe Thr Lys Gly Tyr Gly Phe Gly Leu Ile Lys Leu Asp Leu Lys
            20                  25                  30

Thr Lys Ser Glu Asn Gly Leu Glu Phe Thr Ser Ser Gly Ser Ala Asn
        35                  40                  45

Thr Glu Thr Thr Lys Val Thr Gly Ser Leu Glu Thr Lys Tyr Arg Trp
    50                  55                  60

Thr Glu Tyr Gly Leu Thr Phe Thr Glu Lys Trp Asn Thr Asp Asn Thr
65                  70                  75                  80

Leu Gly Thr Glu Ile Thr Val Glu Asp Gln Leu Ala Arg Gly Leu Lys
                85                  90                  95

Leu Thr Phe Asp Ser Ser Phe Ser Pro Asn Thr Gly Lys Lys Asn Ala
            100                 105                 110

Lys Ile Lys Thr Gly Tyr Lys Arg Glu His Ile Asn Leu Gly Cys Asp
            115                 120                 125

Met Asp Phe Asp Ile Ala Gly Pro Ser Ile Arg Gly Ala Leu Val Leu
130                 135                 140

Gly Tyr Glu Gly Trp Leu Ala Gly Tyr Gln Met Asn Phe Glu Thr Ala
145                 150                 155                 160

Lys Ser Arg Val Thr Gln Ser Asn Phe Ala Val Gly Tyr Lys Thr Asp
                165                 170                 175

Glu Phe Gln Leu His Thr Asn Val Asn Asp Gly Thr Glu Phe Gly Gly
            180                 185                 190

Ser Ile Tyr Gln Lys Val Asn Lys Lys Leu Glu Thr Ala Val Asn Leu
        195                 200                 205

Ala Trp Thr Ala Gly Asn Ser Asn Thr Arg Phe Gly Ile Ala Ala Lys
    210                 215                 220

Tyr Gln Ile Asp Pro Asp Ala Cys Phe Ser Ala Lys Val Asn Asn Ser
225                 230                 235                 240

Ser Leu Ile Gly Leu Gly Tyr Thr Gln Thr Leu Lys Pro Gly Ile Lys
                245                 250                 255

Leu Thr Leu Ser Ala Leu Leu Asp Gly Lys Asn Val Asn Ala Gly Gly
            260                 265                 270

His Lys Leu Gly Leu Gly Leu Glu Phe Gln Ala
        275                 280

<210> SEQ ID NO 22
<211> LENGTH: 283
<212> TYPE: PRT
<213> ORGANISM: Rattus norvegicus

<400> SEQUENCE: 22

Met Ala Val Pro Pro Thr Tyr Ala Asp Leu Gly Lys Ser Ala Arg Asp
1               5                   10                  15

Val Phe Thr Lys Gly Tyr Gly Phe Gly Leu Ile Lys Leu Asp Leu Lys
            20                  25                  30

Thr Lys Ser Glu Asn Gly Leu Glu Phe Thr Ser Ser Gly Ser Ala Asn
        35                  40                  45

Thr Glu Thr Thr Lys Val Asn Gly Ser Leu Glu Thr Lys Tyr Arg Trp
    50                  55                  60

Thr Glu Tyr Gly Leu Thr Phe Thr Glu Lys Trp Asn Thr Asp Asn Thr
65                  70                  75                  80

Leu Gly Thr Glu Ile Thr Val Glu Asp Gln Leu Ala Arg Gly Leu Lys
                85                  90                  95

Leu Thr Phe Asp Ser Ser Phe Ser Pro Asn Thr Gly Lys Lys Asn Ala
            100                 105                 110

Lys Ile Lys Thr Gly Tyr Lys Arg Glu His Ile Asn Leu Gly Cys Asp
        115                 120                 125

Val Asp Phe Asp Ile Ala Gly Pro Ser Ile Arg Gly Ala Leu Val Leu
    130                 135                 140

Gly Tyr Glu Gly Trp Leu Ala Gly Tyr Gln Met Asn Phe Glu Thr Ser
145                 150                 155                 160

Lys Ser Arg Val Thr Gln Ser Asn Phe Ala Val Gly Tyr Lys Thr Asp
                165                 170                 175

Glu Phe Gln Leu His Thr Asn Val Asn Asp Gly Thr Glu Phe Gly Gly
            180                 185                 190

Ser Ile Tyr Gln Lys Val Asn Lys Lys Leu Glu Thr Ala Val Asn Leu

```
                195                 200                 205
Ala Trp Thr Ala Gly Asn Ser Asn Thr Arg Phe Gly Ile Ala Ala Lys
    210                 215                 220

Tyr Gln Val Asp Pro Asp Ala Cys Phe Ser Ala Lys Val Asn Asn Ser
225                 230                 235                 240

Ser Leu Ile Gly Leu Gly Tyr Thr Gln Thr Leu Lys Pro Gly Ile Lys
                245                 250                 255

Leu Thr Leu Ser Ala Leu Leu Asp Gly Lys Asn Val Asn Ala Gly Gly
            260                 265                 270

His Lys Leu Gly Leu Gly Leu Glu Phe Gln Ala
        275                 280

<210> SEQ ID NO 23
<211> LENGTH: 18
<212> TYPE: RNA
<213> ORGANISM: Artificial Sequence
<220> FEATURE:
<223> OTHER INFORMATION: Oligonucleotide

<400> SEQUENCE: 23
gcaagaucau cauuagaa                                                    18

<210> SEQ ID NO 24
<211> LENGTH: 18
<212> TYPE: RNA
<213> ORGANISM: Artificial Sequence
<220> FEATURE:
<223> OTHER INFORMATION: Oligonucleotide

<400> SEQUENCE: 24
guaguaaucu uuaccuuu                                                    18

<210> SEQ ID NO 25
<211> LENGTH: 18
<212> TYPE: RNA
<213> ORGANISM: Artificial Sequence
<220> FEATURE:
<223> OTHER INFORMATION: Oligonucleotide

<400> SEQUENCE: 25
gggaggagag gacaaauu                                                    18

<210> SEQ ID NO 26
<211> LENGTH: 18
<212> TYPE: RNA
<213> ORGANISM: Artificial Sequence
<220> FEATURE:
<223> OTHER INFORMATION: Oligonucleotide

<400> SEQUENCE: 26
cuccuguuua auuucuac                                                    18

<210> SEQ ID NO 27
<211> LENGTH: 18
<212> TYPE: RNA
<213> ORGANISM: Artificial Sequence
<220> FEATURE:
<223> OTHER INFORMATION: Oligonucleotide
```

```
<400> SEQUENCE: 27
agaugagaau cagugaga                                              18

<210> SEQ ID NO 28
<211> LENGTH: 18
<212> TYPE: RNA
<213> ORGANISM: Artificial Sequence
<220> FEATURE:
<223> OTHER INFORMATION: Oligonucleotide

<400> SEQUENCE: 28
uuagucacuc ugcuuuau                                              18

<210> SEQ ID NO 29
<211> LENGTH: 11
<212> TYPE: PRT
<213> ORGANISM: Artificial Sequence
<220> FEATURE:
<223> OTHER INFORMATION: TAT peptide

<400> SEQUENCE: 29

Tyr Gly Arg Lys Lys Arg Arg Gln Arg Arg Arg
1               5                   10

<210> SEQ ID NO 30
<211> LENGTH: 13
<212> TYPE: PRT
<213> ORGANISM: Artificial Sequence
<220> FEATURE:
<223> OTHER INFORMATION: 14-3-3 binding motif

<400> SEQUENCE: 30

Ser Lys Ser Arg Val Thr Gln Ser Asn Phe Ala Val Gly
1               5                   10

<210> SEQ ID NO 31
<211> LENGTH: 13
<212> TYPE: PRT
<213> ORGANISM: Artificial Sequence
<220> FEATURE:
<223> OTHER INFORMATION: 14-3-3 motif of hVDAC1

<400> SEQUENCE: 31

Ala Lys Ser Arg Val Thr Gln Ser Asn Phe Ala Val Gly
1               5                   10
```